United States Patent
Robert

(10) Patent No.: US 10,124,083 B2
(45) Date of Patent: Nov. 13, 2018

(54) SANITIZER WITH AN ION GENERATOR AND ION ELECTRODE ASSEMBLY

(71) Applicant: DM TEC, LLC, Livonia, MI (US)

(72) Inventor: Michael E. Robert, Farmington Hills, MI (US)

(73) Assignee: DM Tec, LLC, Farmington Hills, MI (US)

( * ) Notice: Subject to any disclaimer, the term of this patent is extended or adjusted under 35 U.S.C. 154(b) by 335 days.

(21) Appl. No.: 15/185,708

(22) Filed: Jun. 17, 2016

(65) Prior Publication Data
US 2016/0367712 A1   Dec. 22, 2016

Related U.S. Application Data

(60) Provisional application No. 62/181,475, filed on Jun. 18, 2015.

(51) Int. Cl.
*A61L 9/22* (2006.01)

(52) U.S. Cl.
CPC .............. *A61L 9/22* (2013.01); *A61L 2209/16* (2013.01); *A61L 2209/211* (2013.01)

(58) Field of Classification Search
USPC ..................................................... 250/423 R
See application file for complete search history.

(56) References Cited

U.S. PATENT DOCUMENTS

| 2,392,808 A | 1/1946 | Chapman |
| 2,928,941 A | 3/1960 | Hicks et al. |
| 3,443,155 A | 5/1969 | Schweriner |
| 3,584,766 A | 6/1971 | Hart |
| 3,609,446 A | 9/1971 | Hursh et al. |
| 3,697,806 A | 10/1972 | Herbert, Jr. |
| 3,816,793 A | 6/1974 | Radloff et al. |

(Continued)

FOREIGN PATENT DOCUMENTS

| CN | 2169935 | 6/1994 |
| CN | 2235509 | 9/1996 |

(Continued)

OTHER PUBLICATIONS

Prutchi et al., "d.i.y. 250 kV High Voltage DC Power Supply with Neat Trick for Switching Polarity," http://www.diyphysics.com/2012/02/09/d-i-y-250-kv-high-voltage-dc-power-supply-with-neat-trick-for-switching-polarity/ (accessed May 8, 2015).

(Continued)

*Primary Examiner* — Kiet T Nguyen
(74) *Attorney, Agent, or Firm* — Craig A. Phillips; Dickinson Wright PLLC

(57) ABSTRACT

A sanitizer with an ion generator and ion electrode assembly are provided. The ion generator is configured to generate ions using an AC voltage and an ion electrode assembly. The ion electrode assembly includes at least one emitter unit adapted for attachment to the ion generator. At least one ion source is attached to the at least one emitter unit for emitting ions. An emitter cover that is flexible has a thickness and extends from a proximal end to a distal end and defines an inner surface and encloses the at least one emitter unit for protecting the at least one ion source and the at least one emitter unit. The inner surface of the emitter cover is in a spaced relationship with the at least one ion source to define an air gap.

40 Claims, 28 Drawing Sheets

(56) References Cited

U.S. PATENT DOCUMENTS

| | | | |
|---|---|---|---|
| 3,828,239 A | 8/1974 | Nagai et al. | |
| 3,840,797 A | 10/1974 | Aggen et al. | |
| 3,866,086 A | 2/1975 | Miyoshi et al. | |
| 3,878,469 A | 4/1975 | Bolasny | |
| 3,943,407 A | 3/1976 | Bolasny | |
| 3,981,695 A | 9/1976 | Fuchs | |
| 4,069,665 A | 1/1978 | Bolasny | |
| 4,282,460 A | 8/1981 | Luz et al. | |
| 4,292,592 A | 9/1981 | Birdwell et al. | |
| 4,301,497 A | 11/1981 | Johari | |
| 4,597,781 A | 7/1986 | Spector | |
| 4,616,300 A | 10/1986 | Santelmann, Jr. | |
| 4,689,715 A | 8/1987 | Halleck | |
| 4,789,801 A | 12/1988 | Lee | |
| 4,893,227 A | 1/1990 | Gallios et al. | |
| 4,974,115 A | 11/1990 | Breidegam et al. | |
| 5,010,869 A | 4/1991 | Lee | |
| 5,055,963 A | 10/1991 | Partridge | |
| 5,317,155 A | 5/1994 | King | |
| 5,452,720 A | 9/1995 | Smith et al. | |
| 5,484,472 A | 1/1996 | Weinberg | |
| 5,930,105 A | 7/1999 | Pitel et al. | |
| 6,201,359 B1 | 3/2001 | Raets | |
| 6,771,519 B2 | 8/2004 | Frus et al. | |
| 7,218,500 B2 | 5/2007 | Adachi | |
| 7,564,671 B2 | 7/2009 | Kato et al. | |
| 7,601,970 B2 | 10/2009 | Lee | |
| 7,649,728 B2 | 1/2010 | Fujita et al. | |
| 7,662,348 B2 | 2/2010 | Taylor et al. | |
| 7,854,900 B2 | 12/2010 | Takeda et al. | |
| 7,920,368 B2 | 4/2011 | Fujiwara et al. | |
| 7,995,321 B2 | 8/2011 | Shimada | |
| 8,009,405 B2 | 8/2011 | Gefter et al. | |
| 8,149,371 B2 | 4/2012 | Oohira | |
| 8,605,407 B2 | 12/2013 | Gefter et al. | |
| 8,773,837 B2 | 7/2014 | Partridge et al. | |
| 8,885,317 B2 | 11/2014 | Partridge | |
| 9,847,623 B2* | 12/2017 | Sunshine | H01T 19/04 |
| 9,950,086 B2* | 4/2018 | Robert | A61L 2/14 |
| 2002/0014410 A1 | 2/2002 | Silveri et al. | |
| 2004/0184975 A1 | 9/2004 | Anno | |
| 2005/0028254 A1 | 2/2005 | Whiting | |
| 2006/0018811 A1 | 1/2006 | Taylor et al. | |
| 2006/0243762 A1 | 11/2006 | Sassoon | |
| 2007/0279829 A1 | 12/2007 | Gefter et al. | |
| 2008/0250928 A1 | 10/2008 | DeSalvo et al. | |
| 2009/0316445 A1 | 12/2009 | Mowrer et al. | |
| 2010/0064545 A1 | 3/2010 | Pollack et al. | |
| 2010/0065535 A1 | 3/2010 | Zheng et al. | |
| 2010/0157503 A1 | 6/2010 | Saito et al. | |
| 2011/0102963 A1 | 5/2011 | Sekoguchi | |
| 2011/0133098 A1 | 6/2011 | Kitagaito et al. | |
| 2011/0150710 A1 | 6/2011 | Tsuda et al. | |
| 2012/0081929 A1 | 4/2012 | Dvorsky | |
| 2012/0200982 A1 | 8/2012 | Partridge | |
| 2012/0224293 A1 | 9/2012 | Partridge et al. | |
| 2012/0240968 A1 | 9/2012 | Schumacher | |
| 2012/0314333 A1 | 12/2012 | Takeda et al. | |
| 2013/0095000 A1 | 4/2013 | Yamamoto et al. | |
| 2013/0201730 A1 | 8/2013 | Luo | |
| 2013/0232807 A1 | 9/2013 | Robert et al. | |
| 2014/0285084 A1 | 9/2014 | Fomani et al. | |
| 2015/0204759 A1* | 7/2015 | Sugiyama | G01N 15/0656 73/114.71 |
| 2016/0104595 A1 | 4/2016 | Nishida et al. | |
| 2016/0263263 A1* | 9/2016 | Robert | A61L 2/14 |

FOREIGN PATENT DOCUMENTS

| | | |
|---|---|---|
| CN | 1536281 | 10/2004 |
| CN | 201311011 | 9/2009 |
| CN | 203423631 | 2/2014 |
| CN | 203481626 | 3/2014 |
| EP | 0368858 | 5/1995 |
| EP | 1637811 | 3/2006 |
| EP | 1625890 | 6/2011 |
| JP | 2001043992 | 2/2001 |
| JP | 2002216994 | 8/2002 |
| JP | 5185250 | 4/2013 |
| WO | 2010144528 | 12/2010 |
| WO | 2013119283 | 8/2013 |

OTHER PUBLICATIONS

"Flyback Transformer," Wikipedia, http://en.wikipedia.org/Wiki/Flyback_transformer (accessed May 8, 2015).

"Basic Single-Output Flyback Converter Circuit Diagram," http://datasheetoo.com (accessed May 15, 2014).

Schmidt et al., "Microfabricated differential mobility spectrometry with pyrolysis gas chromatography for chemical characterization of bacteria," Anal Chem. 2004, Abstract.

International Search Report, dated Jun. 25, 2015 (PCT/US2015/020288).

Gadri, Ben et al.; Sterilization and plasma processing of room temperature surfaces with a one atmasphere uniform glow discharge plasma (OAUGDP); Surface & Coatings Technology; vol. 131, pp. 528-542 (2000).

* cited by examiner

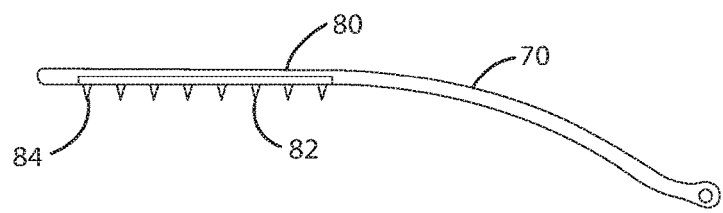
Fig. 10
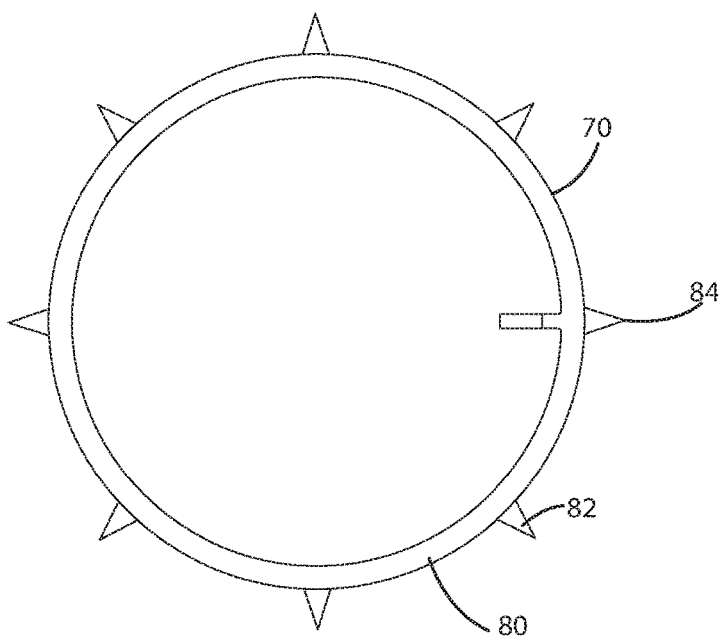 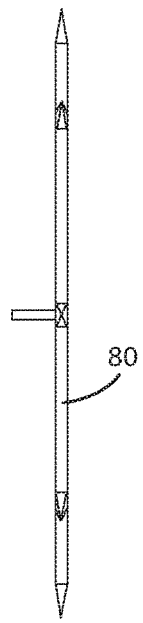
Fig. 11 Fig. 12

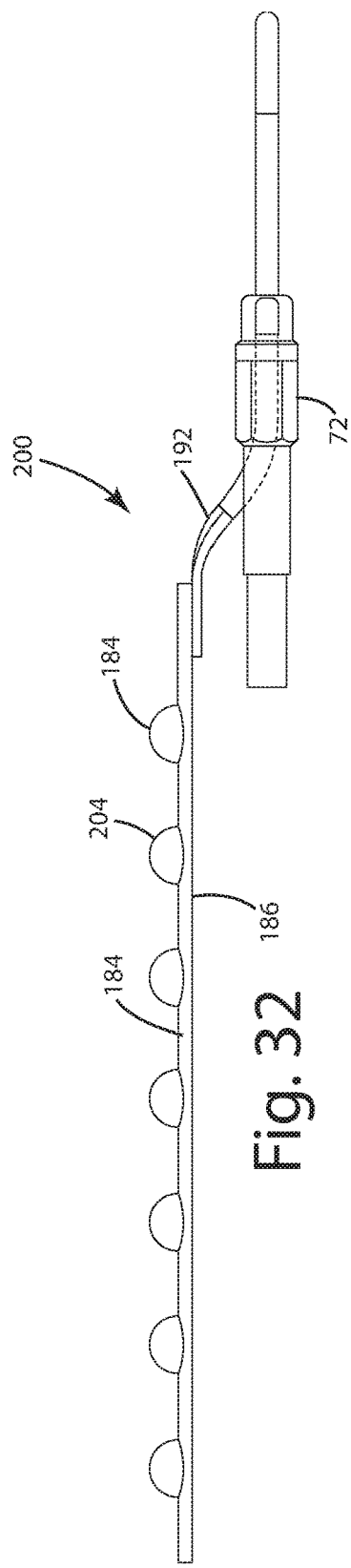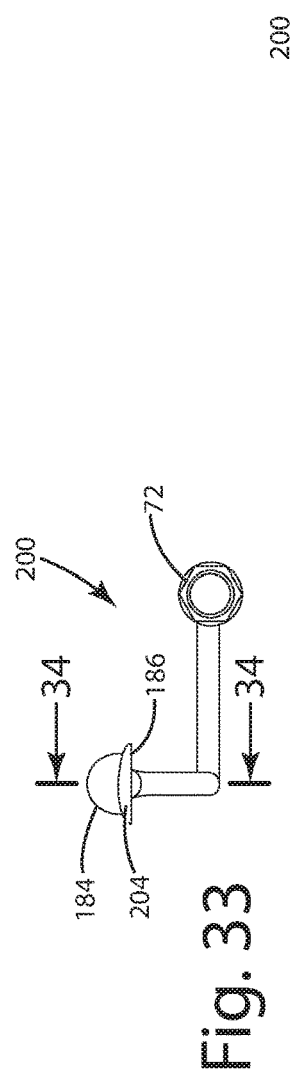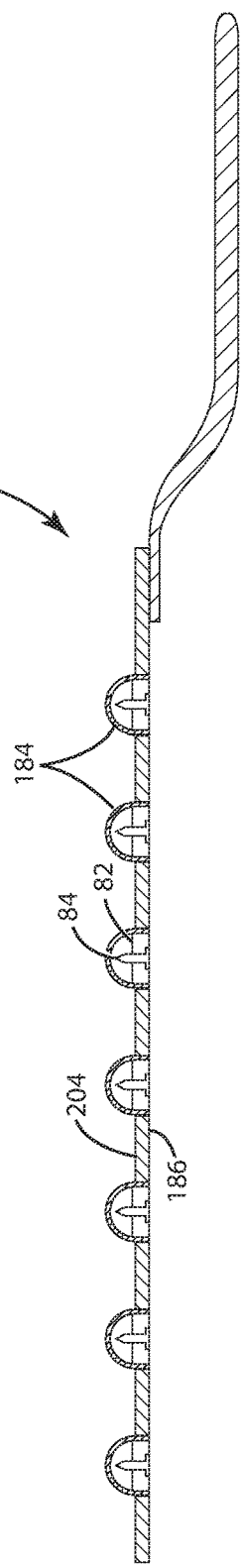
Fig. 32
Fig. 33
Fig. 34

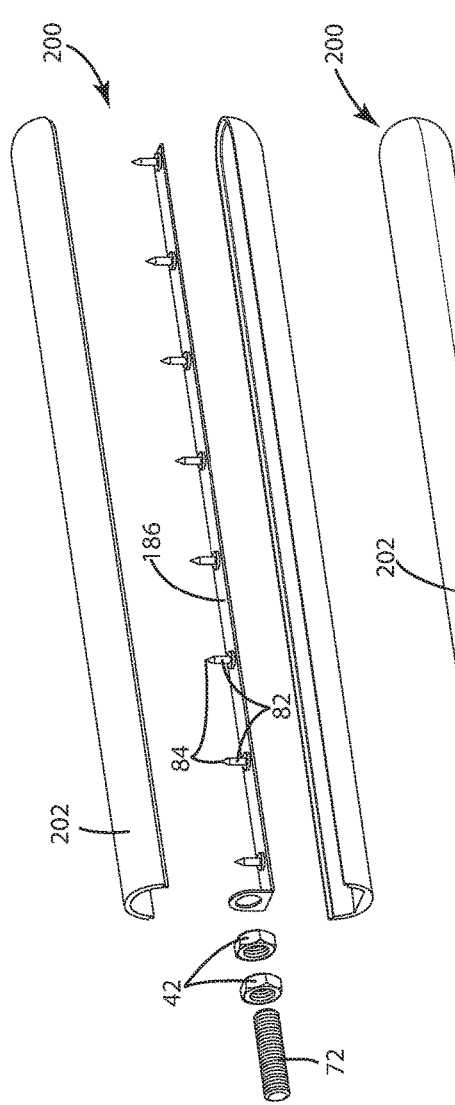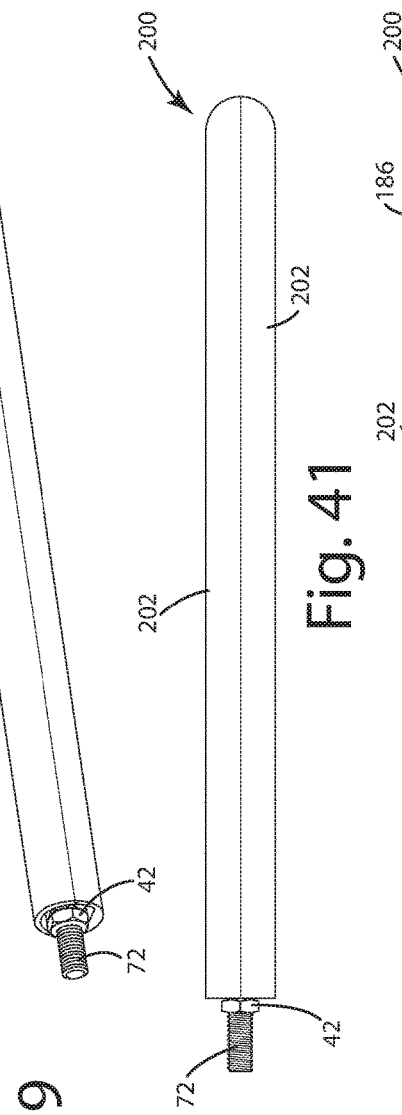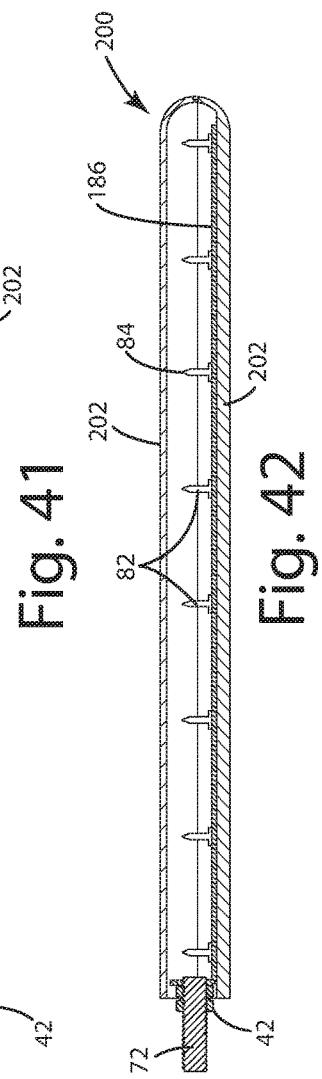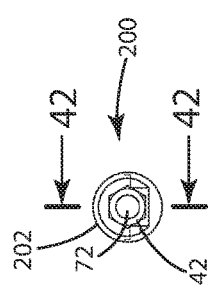

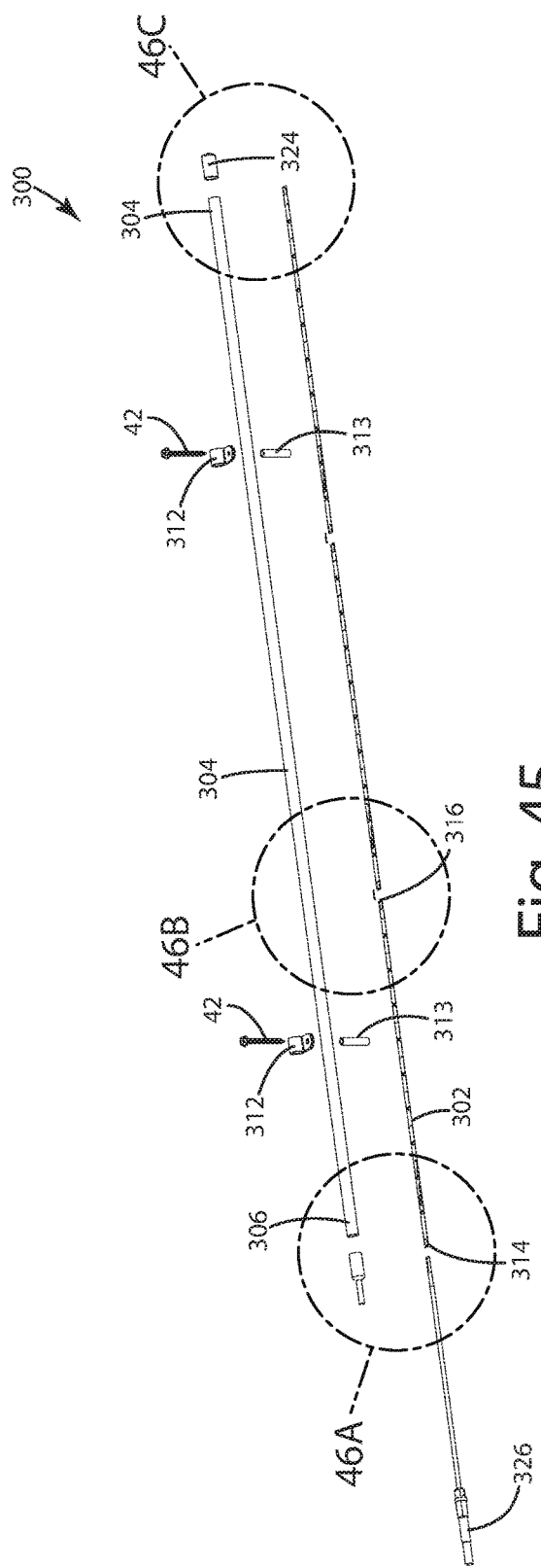
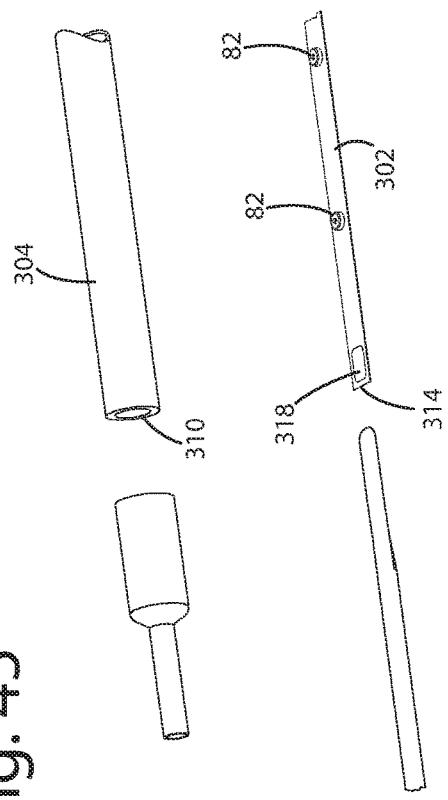
Fig. 45
Fig. 46A

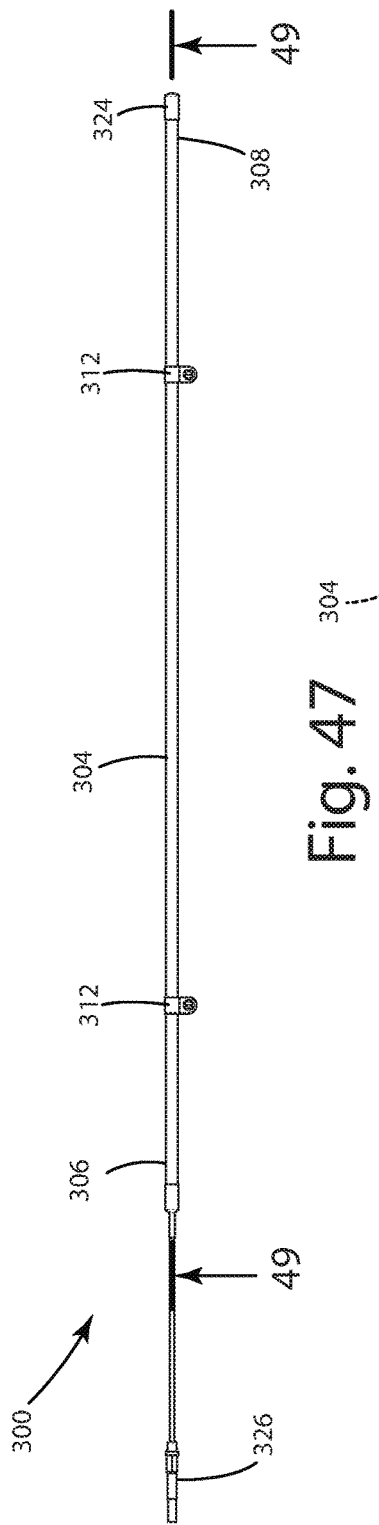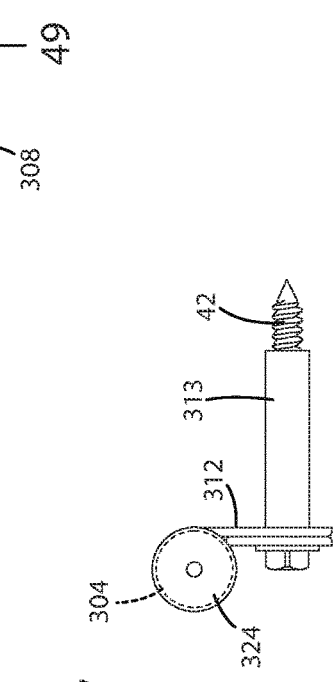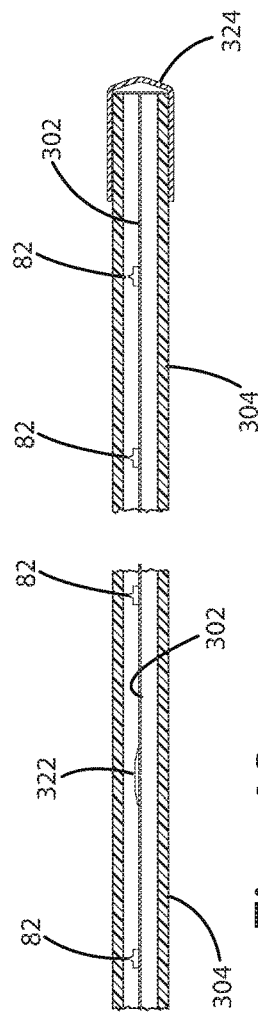

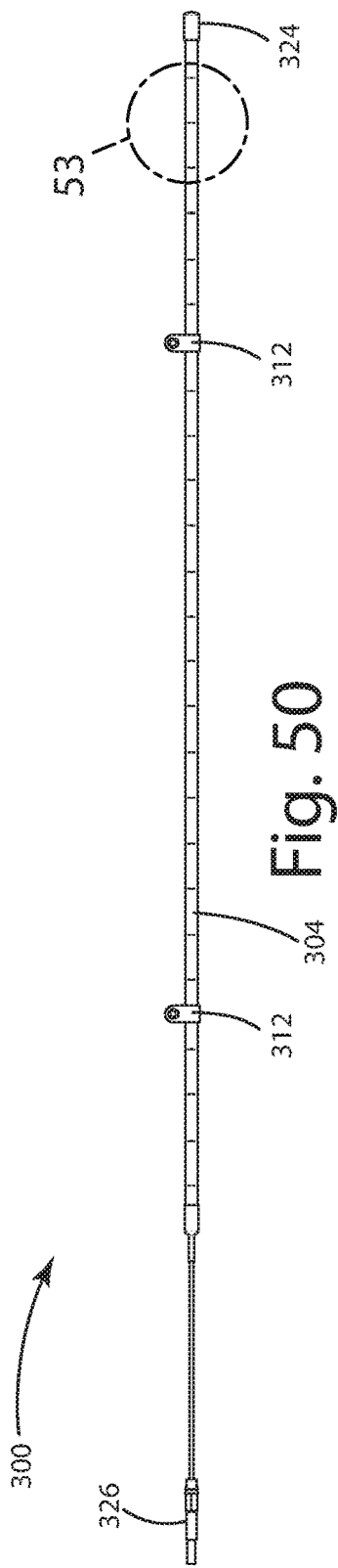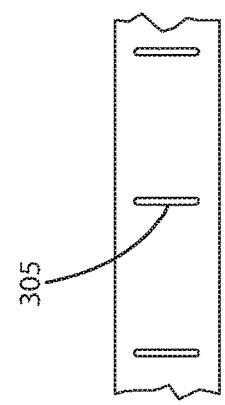

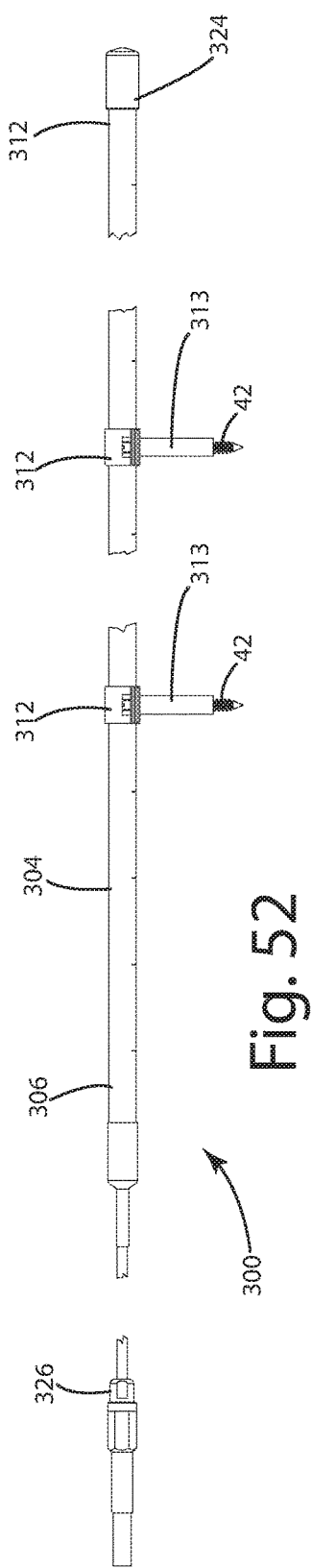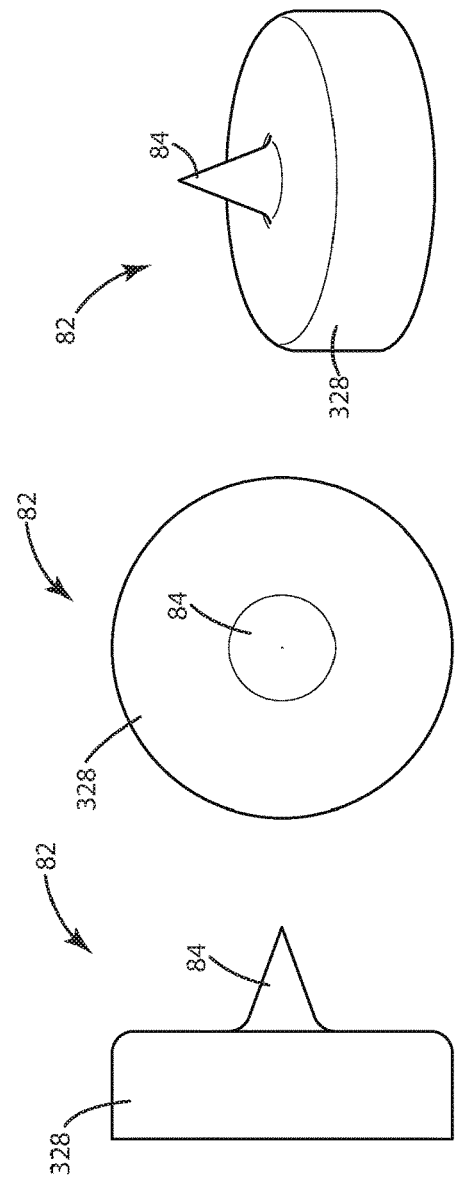

SANITIZER WITH AN ION GENERATOR AND ION ELECTRODE ASSEMBLY

CROSS REFERENCE TO RELATED APPLICATION

This application claims the benefit of U.S. Provisional Application Ser. No. 62/181,475 filed Jun. 18, 2015, which is incorporated herein by reference in its entirety.

BACKGROUND OF THE INVENTION

1. Field of the Invention

The present invention is directed to a sanitizer for sanitizing various surfaces including hands, hardware, fixtures, appliances, including the interior of refrigerators, countertops, equipment, utensils, HVAC (heating, ventilation, and air conditioning) systems, including ductless mini-split systems, and specifically to ion generators and ion electrode assemblies that do not use sacrificial anodes and cathodes, and do not require the addition of chemicals, and do not produce ozone to sanitize.

2. Description of the Prior Art

It is well known that many infectious diseases and pathogens are communicated through touch or contact. Therefore, commonly touched items in public areas and facilities such as doorknobs, handles, fixtures, and other surfaces may spread such infectious diseases and pathogens. People are particularly concerned with touching various surfaces in public restrooms even communal restrooms at a work place due to actual or perceived sanitary conditions of those restrooms and the users of the restrooms. However, contact with door handles, knobs and other fixtures related to the restroom is many times unavoidable. Other exemplary surfaces that may be unavoidable and be contaminated with pathogens from people or other sources including food preparation may include drinking fountains, kitchen counter tops, shared appliances, refrigerator shelves, and nearly any other surface that multiple people may contact. Therefore, many people generally find it desirable to avoid or minimize contact with such surfaces when possible.

People are particularly concerned with the cleanliness of surfaces after washing their hands or before the eating of food. However, touching many of the surfaces in a restroom after washing hands or in a kitchen while preparing food particularly in a work place kitchen is unavoidable. For example, in most restrooms as a person must touch the handle of the door to exit a restroom, touch the same faucet handle used to turn on the water or to turn off the faucet, which may recontaminate the just cleaned hands. In a kitchen, other than door and fixture handles such as faucets, a refrigerator door handle or the surface of a microwave and light switches may all be contaminated with various pathogens. Some people use extra paper towels to cover and touch handles of door or faucets in certain situations, however, generally this is wasteful and adds expense for the facility including increased paper cost as well as increased labor cost for replacing the paper products more frequently.

In addition, many people have desired to sanitize the air exiting from HVAC systems, fans, as well as sanitize the HVAC system itself. The air within a building may include various pathogens and other harmful items, which is desirable to remove. In addition, the HVAC system itself may form an environment that is conducive to harmful pathogens growing, such as due to the moisture present, as well as the air that moves through the system. A number of prior methods have been proposed, all having limited success or significant drawbacks in sanitizing various surfaces, particularly on individual's hands, especially for individuals who have chemical sensitivity issues. The first method is generally more frequent cleaning of such surfaces, however, this increases time and labor costs and generally people are distrustful that the surfaces have been properly cleaned. In addition, even if the cleaning was thorough and no pathogens exist on the surface, the very first contact by a person may place undesirable infectious agents or pathogens on the surface and any subsequent users may come in contact with such infectious agents or pathogens. Therefore, the more frequent cleanings do not solve the problem of contaminated surfaces.

Some facilities provide various cleaning wipes, liquids, or sponges that may be used for cleaning of the surface by a user. While these are generally capable of cleaning the surface, the use is limited to a person actually using them. A big disadvantage to these wipes, liquids, or sponges is that they require frequent replacement thereby increasing the cost for the facility. Many times these anti-bacterial sprays, liquids or wipes are empty creating an undesirable situation for the person using the facility. In addition, if such sprays, liquids and the like are improperly used, the pathogens may still exist and not be substantially reduced.

To address the above problems, some manufacturers have introduced various electronic chemical sanitizers that with little to no interaction with a user at regular intervals or upon activation of a sensor, sprays a liquid on the desired surface, or upon sensing someone placing objects or body parts, such as hands in a specified area. In addition to the increased maintenance cost as well as product cost of replacing the battery and the chemical or wet material, generally most people find it undesirable to touch a moist or damp surface such as a moist or damp door handle, even if the moisture or liquid is a sanitizing chemical. In addition, many people do not like the smell or have various chemical allergies to the chemical being used on the door handle, making it difficult to use that facility. More specifically, such as in an office setting, if one worker has a chemical allergy to the cleaning device that is being used, which on a timed or activated interval sprays a door handle, it may prevent further use in that facility. To address the problems some people have proposed using ultraviolet sanitizers that when positioned or placed over a non-porous surface effectively sterilizes and sanitizes the surface. While such devices prevent the spread of pathogens passed on by contact by direct exposure to ultraviolet light, these devices generally are power intensive and require frequent battery changes or recharging unless they are hardwired into a facility's electrical system. Therefore, for doors, wherein they are controlled by a preprogrammed timer or motion sensing, their useful life is relatively limited requiring regular maintenance by the facility thereby raising costs. Many people are also concerned regarding sticking their hands on a door handle to open it where it will be bathed in ultraviolet light. The positioning of many of these devices is above a door handle or counter top which places it high enough that smaller people, such as children, may inadvertently look directly at the ultraviolet lamp which is undesirable and could cause vision issues. Therefore, the implementation of these devices as sanitizers for various fixtures that cannot fit in an enclosure has been limited due to their serious drawbacks.

To address the shortcomings with various chemical and ultraviolet light sanitizers, some manufacturers have introduced ozone sanitizers, which is known to be a potent sanitizer for various surfaces as it is a highly reactive oxidizer. Ozone works well at killing various pathogens, and unlike chemical sanitizers, leaves no chemical residue on the treated surfaces. Ozone has been highly desirable for use in food processing plants, but has had limited other practical applications. A sanitizing processing system is generally of limited use because it must control the output of ozone in a sealed environment. Therefore, it is used in large industrial only settings and have not been successfully implemented in households or small commercial applications. More specifically, the application of ozone sanitizing systems has been extremely limited by the more recent understanding that ozone may cause various health issues including according to the EPA, respiratory issues such as lung function, decrements, inflammation and permeability, susceptibility to infection, cardiac affects and more seriously respiratory symptoms including medication use, asthma attacks and more. The respiratory symptoms can include coughing, throat irritation, pain, burning, or discomfort in the chest when taking a deep breath, chest tightness, wheezing or shortness of breath. For some people, more acute or serious symptomatic responses may occur. As the concentration at which ozone effects are first observed depends mainly on the sensitivity of the individual, even some parts per billion exposure may cause noticeable issues. Therefore, other than commercial environments where the ozone application must be specifically controlled and these systems are not desirable for a broader implementation in homes, work places and other facilities, where the ozone is not easily contained, such as functioning as a door handle sanitizer for an operational door.

Existing sanitizers or ozone devices require a method of propelling the ions or ozone away from the device. As such, many of these devices use fans, compressed air, or other mechanisms for dispersing the ions. One problem with such systems is that in applications where an external power source is not readily available, batteries for fans, and other means of propulsion such as $CO_2$ canisters must be replaced on a fairly regular basis. In mechanisms using a fan powered by battery, the fans substantially limits the life of the battery to the point where it needs to be replaced weekly or even bi-weekly in certain environments. Other systems using compressed air or $CO_2$ require replacement or recharging of the cartridges or tanks on a regular basis. In addition, any sanitizer requiring a mechanism for propelling the ions outward such as the battery-powered fans or compressed air stop efficiently functioning, without the mechanism for propulsion.

Bipolar ionizers use a high voltage to create an electric field across two discharge points. One point creates positive ions and the other point creates negative ions. It is well known that as the number of points increases, the amount of ions that may be generated due to the nature of electrical fields and increase in surface area from using multiple points, is reduced. More specifically, the use of a single point requires that all of the electrical fields will pass through that point. As such, the production of ions is maximized by use of a single point. Traditionally, multiple points as ion sources were discouraged to maximize ion production. In addition, Bipolar ionizers use a high voltage to create an electric field across two discharge points. One point creates positive ions and the other point creates negative ions. (Note, multiple discharge points for positive and multiple discharge points for negative are acceptable). The most common methods of creating the required voltage are either a flyback transformer or a voltage multiplier circuit or a combination of the two, as illustrated in FIG. 34. These circuits are well known. Because the high voltage output is direct current (DC), two discharge points are required—one for positive and the other for negative. Most implementations of a flyback transformer use feedback from a secondary winding on the transformer to create a resonator that switches the primary side of the transformer on and off. While this circuit is simple and cost effective, it often takes long periods of time for the circuit to stabilize and reach its full output, as illustrated in the graph in FIG. 35, which shows just a small portion of the output at the peak, thereby limiting generation of ions.

In addition, certain pathogens are becoming resistant to various chemicals used in chemical sanitizers. For example, in the medical field, one of the biggest problems facing hospitals and clinics is pathogens that are resistant to various chemicals.

A number of ion generators also require thermal plasma to function. Thermals plasma ion generators produce ions, but are extremely hot, limiting their effective use in close proximity to humans, such as use in a hand sanitizer. As with any ions created by an ion generator, many of the ions are unstable and quickly convert back, limiting the effective range of the ions that are useful in sanitizing surfaces, including hands of various pathogens, yet it is desirable to space hands well away from any thermal plasma field. Therefore, thermal plasma devices have serious design constraints when used to sanitize surfaces, such as door handles and other fixtures that are in regular human contact, and any sanitizing of human body surfaces, such as hands in thermal plasma is not advisable and should be avoided. In addition, as stated above, many ion generators operate in a similar manner to ozone generators. Therefore, thermal plasma is generally undesirable because it may cause corona discharge, which is related to ozone production.

Another drawback to ion generators that use a thermal plasma is the high power consumption required to generate the thermal plasma. In general, any thermal plasma ion generator must be used connected to the power grid. Battery life of a thermal ion generator would be so short or require such large capacity batteries, therefore requiring large volumes of space, any use of the ion generator remote from the power grid would be impractical, and the maintenance requirements would be extremely high in relation to replacing or recharging the batteries. Therefore, ion generators that use thermal plasma are generally not useful to attach to doors, walls or other locations where it is difficult to connect them to the power grid. In addition, even if a thermal plasma ion generator may be placed in a position to connect to the power grid, the installation cost is typically high, and the high power consumption is expensive.

Most ion generators only generate a single type of ion, typically only negative ions. Any ion device only generating a single type of ion or more specifically, a single type of charge for the ions are generally not as effective as ion generators producing both positive and negative ions in killing pathogens to sanitize surfaces. Therefore, a need exists for an ion generator that is bipolar, not just monopolar, and more specifically, an ion generator that produces sufficient quantities of positive and negative ions.

Some sanitizers require expensive sacrificial anodes or cathodes. Sacrificial anodes or cathodes must be replaced, and in addition, sacrificial anodes or cathodes put pieces of the anode or cathode in the environment, typically as ions in a fluid, which may subject the ion generator to numerous additional regulations. In addition, if either the cathodes, anode or fluid is depleted, the sanitizer ceases to function as desired.

Similar to the many drawbacks with hand sanitizers, to date no one has found a sanitizing system or assembly that sufficiently sanitizes HVAC systems or other air handling devices, such as fans, make up air systems and the like. As HVAC systems pull in air from the building that includes pathogens, the HVAC may distribute such pathogens throughout the environment in which the HVAC system operates, such as through the ductwork. While many manufactures have tried to eliminate this issue by installing various filters of ever increasing quality, these filters are generally limited to ensure sufficient airflow, allowing most pathogens to pass through. In fact, the filter itself may become a habitat for various pathogens, creating even more problems. As such, filtering the air, while a good idea, in itself does not provide sufficient protection from airborne pathogens in most HVAC systems.

In addition, the environment in most HVAC systems, particularly ductless mini-split systems is conducive to growing various pathogens. For example, the moisture on the coils of an HVAC system, whether in a house, commercial building, vehicle, or anywhere else may create an environment for the pathogens and other unwanted organisms, such as mold, spores, bacterial and other undesirable items. There currently is no easy way to clean the coils of an air conditioning unit in most HVAC systems, particularly in vehicles and residential systems, as well as most commercials systems. As these systems cannot be cleaned, are conducive to the growth of harmful organisms, and by their very nature of moving air, are exposed to high levels of pathogens and the like, it is desirable to be able to clean them.

Some manufactures have suggested placing ozone generators in the systems, but ozone has been found to be harmful even in minor quantities to humans, so these prior systems are undesirable. Some manufactures have suggested putting an ion generating in the HVAC systems. Current ion generating systems use a glass electrode with wire mesh to create a dielectric barrier. These glass tube electrodes are extremely fragile, extremely expensive, and do not have a long life span, thereby requiring replacement at frequent intervals. For example, most glass dielectric electrodes cost over $100 each, and can easily be ruined by vibration. As such HVAC systems with their vibrations are not conducive to glass electrode ion systems, even when ignoring their high purchase price and lack of longevity. Glass electrode tubes are generally large and bulky and cannot fit in vehicles or ductless mini split systems. Therefore, there is a need for a better ion system, particularly one that can operate even in vehicles and ductless mini-split systems.

To address some of the concerns of glass electrodes, some manufactures have introduced metal bars that are suspended in the air ducts. These metal bars are usually long, large and difficult to position in system, other than large air ducts. As such, they cannot be used in vehicles, and ductless mini split systems, as they do not fit or when reduced in size do not produce enough ions to be effective. In addition, these metal bars operate at extremely high voltage and with enough amperage to require that during operation they cannot be touched by individuals without danger of possible electrocution or injury. As metal bars are conductive, the risk also may occur if the bar is improperly installed and creates an electrical connection to the metal ductwork or other items of an HVAC system.

Therefore, there is a need for an effective ion generator for use in sanitizers, hand dryers, HVAC systems and other appliances and apparatuses that do not include the above identified limitations.

SUMMARY OF THE INVENTION

The present invention is directed to a sanitizer for sanitizing various surfaces including hands, hardware, fixtures, appliances, countertops, equipment, utensils and more and more specifically to an ozone-free sanitizer and yet more specifically to an electronic sanitizer using alternating current (AC), not direct current (DC) voltage at the ion sources with a single ion electrode and a ground electrode, and a sanitizer that uses liquid, such as water to enhance the sanitizing effect of the plasma field, and more specifically, to a bipolar ion generator, capable of generating both positive and negative ions.

The present invention is also directed to an ion electrode assembly for use with the ion generating device that is safe to touch, easy to install without injury of touching carbon brushes or needles used to generate ions and very surprisingly, and ion generating device that does not include a special ground electrode proximate to the ion generating electrode, yet creates more useable ions in a weaker electrical field.

The present invention is directed to a sanitizer having an ion generator and a fluid reservoir. The ion generator includes a controller and at least one electrode. The fluid reservoir is in fluid communication with a nozzle and wherein the nozzle is proximate the at least one electrode and wherein the at least one electrode is not a sacrificial electrode. The ion electrode produces ions that are expelled toward the desired surface, including hands, gloves countertops, etc. and does not produce ions in the fluid in the fluid reservoir. The fluid is typically water, but other fluids may be used.

The at least one electrode includes an ion electrode and a ground electrode and the ion electrode includes at least one ion source. The ion electrode includes a plurality of ion sources and wherein each of the ion sources is configured as a point. In contrast to the prior art which teaches a single point, the inventors have found it advantageous to use multiple points. The ion electrode is spaced from the ground electrode. The nozzle or the housing or another conductive material may act as the ground electrode. The nozzle is configured relative to the ion electrode, such that during operation a fluid exiting the nozzle substantially passes through a plasma field generated by the ion electrode.

The sanitizer in place of a motion sensor or IR sensor may instead or in addition include an actuating lever. The ground electrode may be located on the actuating lever. The ion electrode is typically proximate to the nozzle. The nozzle and fluid dispensing system may measure and provide a specified amount of fluid passing through the plasma field, such as in response to motion or the actuation of the actuating lever. If the sanitizer includes a motion sensor and the fluid is dispensed from the nozzle in response to an input from the motion sensor to a controller.

The sanitizer in addition to the controller may be hardwired into a building power supply or may in addition or instead further include a battery in electrical communication with the controller. The ion electrode may have ion sources spaced 6-51 mm apart. Each of the ion sources extend to a point on a ring forming the ion electrode, and may face any direction, such as inward, outward, in line with the axis of the ring or generally as illustrated are pointed toward the nozzle.

The sanitizer may include at least one electrode that includes a positive ion electrode and a negative ion electrode at any given time. The at least one electrode includes an ion electrode fluctuating between positive and negative charge at 1-100 Hz.

The sanitizer of fluid from the fluid reservoir is not heated, and is expected to be approximately ambient temperature.

In addition, the present includes a method of sanitizing comprising providing a sanitizer with a fluid reservoir in communication with a nozzle, and an ion generator including at least one ion electrode proximate to the nozzle; generating a non-thermal plasma field with the ion electrode; and dispensing a fluid through the nozzle while generating the non-thermal plasma field, and wherein the fluid passes through the non-thermal plasma field.

It is an aspect of the present disclosure to provide an ion electrode assembly including at least one emitter unit adapted for attachment to an ion generator. At least one ion source is attached to the at least one emitter unit for emitting ions. An emitter cover that is flexible and has a thickness and defines an inner surface that is continuous and encloses the at least one emitter unit for protecting the at least one ion source and the at least one emitter unit. The inner surface of the emitter cover is in a spaced relationship with the at least one ion source to define an air gap.

According to another aspect of the disclosure, an ion electrode assembly is provided. The ion electrode assembly includes at least one emitter unit adapted for attachment to an ion generator. At least one ion source is attached to the at least one emitter unit for emitting ions. At least one emitter cover that has a thickness and defines an inner surface and encloses the at least one emitter unit for protecting the at least one ion source and the at least one emitter unit. The inner surface of the emitter cover is in a spaced relationship with the at least one ion source to define an air gap.

According to yet another aspect of the disclosure, an ion electrode assembly is provided. The ion electrode assembly includes an ion generator and at least one emitter unit adapted for attachment to the ion generator. At least one ion source is attached to the at least one emitter unit for emitting ions. An emitter cover that is flexible has a thickness and defines an inner surface that is perforated and encloses the at least one emitter unit for protecting the at least one ion source and the at least one emitter unit. The inner surface of the emitter cover is in a spaced relationship with the at least one ion source to define an air gap.

It is another aspect of the present disclosure that the emitter cover of the ion electrode assembly is a tube or a dome. The at least one emitter unit can include a plurality of emitter units coupled to one another with at least one jumper. The emitter cover can extend from a proximal end to a distal end with an emitter electrical connector disposed at the proximal end and an end cap disposed on the distal end. The emitter cover can be plastic and may either be continuous or perforated. The thickness of the emitter cover may also be reduced proximate the at least one ion source.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 10 is a top view of an exemplary ion electrode;
FIG. 11 is a top view of an exemplary ion electrode;
FIG. 12 is a side view of the ion electrode in FIG. 11;
FIG. 32 is a side view of a new ion electrode assembly;
FIG. 33 is an end view of the new ion electrode assembly in FIG. 32;
FIG. 34 is a sectional view of the new ion electrode assembly taken along lines A-A in FIG. 33;
FIG. 38 is an exploded perspective view of an ion electrode assembly;
FIG. 39 is a perspective view of the assembled ion electrode assembly in FIG. 38;
FIG. 40 is an end view of the ion electrode assembly in FIG. 38;
FIG. 41 is a side view with hidden lines showing the interior components of the ion electrode assembly;
FIG. 42 is a cross sectional view of the ion electrode assembly taken along lines A-A in FIG. 40;

FIG. 45 is an exploded perspective view of an ion electrode assembly;

FIGS. 46A-46C are enlarged partial views of the ion electrode assembly of FIG. 45;

FIG. 47 is a side view of the ion electrode assembly of FIG. 45;

FIG. 47 is a side view of the ion electrode assembly of FIG. 45;

FIG. 48 is an end view of the ion electrode assembly of FIG. 45;

FIG. 49 is a cross-sectional view of the ion electrode assembly of FIG. 45;

FIG. 50 is a side view of an ion electrode assembly;

FIG. 51 is an enlarged partial view of the ion electrode assembly of FIG. 50;

FIG. 52 is a broken side view of the ion electrode assembly of FIG. 45;

FIGS. 53A-53C are views of an ion source of the ion electrode assembly of FIG. 45.

DESCRIPTION OF THE ENABLING EMBODIMENT

Figure 1:
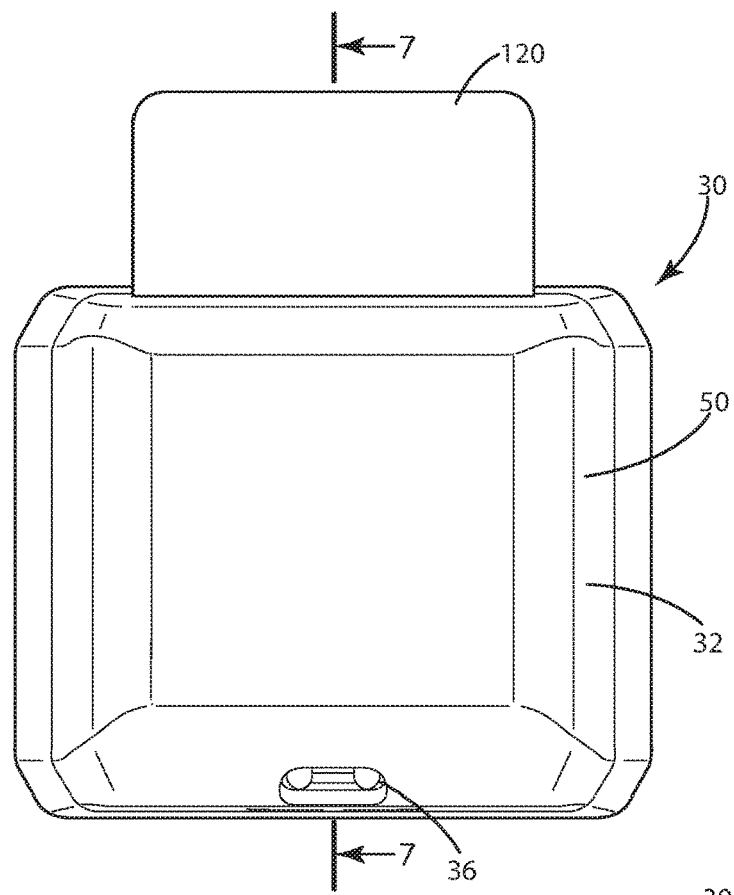
FIG. 1 is a front view of an exemplary sanitizer.

The present invention is generally directed to a sanitizer for sanitizing various surfaces including hands. The ion generator for the sanitizer as described below generally produces charged ions that are expelled by the sanitizer toward an object or surface to be sanitized using the electrical field of the ion generator. The ion generator is specifically configured to avoid the production of ozone and should not be confused with ozone sanitizers. Instead, the present invention provides a compact ion sanitizer that avoids the production of ozone during normal operation and therefore sanitizes without any ozone. Careful configuration of the ion sources and voltage is required to avoid the production of ozone.

Bipolar ionization of a gas creates plasma that is not in thermodynamic equilibrium because the ion temperature is lower than the electron temperature. This plasma is commonly referred to as 'cold plasma' or 'non-thermal plasma' because it occurs at room temperatures. Plasmas in thermodynamic equilibrium require much more energy and occur at significantly higher temperatures. Cold plasma has many benefits that will be discussed in greater detail. These benefits include, but are not limited to the ability to kill harmful pathogens including bacteria, *mycoplasma*, viruses, and mold. Additionally, cold plasma may help with a reduction of Volatile Organic Compounds (VOC's) and a reduction of particulates in the air including known allergens. Furthermore, cold plasma also reduces or eliminates static electricity in the air.

An ion is a molecule that is either positively or negatively charged. Most ions are unstable. A negative ion has at least one extra electron to give up in order to become stable. A positive ion is missing at least one electron that it must gain to become stable. It is believed that such instability of ions creates the desired electrochemistry capable of killing harmful pathogens including, but not limited to bacteria, *mycoplasma*, viruses, and mold.

Ions created in the air are referred to as 'air ions' or sometimes, simply 'ions'. Air ions may be classified by their charge and mobility. An air ion will move in the presence of an electric field due to its charge. The velocity of the air ion is proportional to the strength and direction of the electric field given in Volts per meter (V/m). With velocity given in m/s:

$$\text{Mobility, } \mu = (m/s)/(V/m) = m2/Vs$$

where; m=distance in meters, s=time in seconds, and V=electrical potential in Volts The drift velocity (Vd) of an air ion is proportional to the Electric Field and inversely proportional to its mass. Therefore, smaller ions in a large electric field will have the greatest drift velocity.

Examples of air ions include small stable negative ions such as an Oxide molecule ion $(O2^-+(H_2O)_n)$, Carbon dioxide ion $(CO_3^-+(H_2O)_n)$, and Nitric acid ion $(NO3^-+(H_2O)_n)$. Other examples of air ions include small stable positive ions such as a Hydrogen ion $(H^++(H_2O)_n)$, and Oxonium ion $(H_3O^++(H_2O)_n)$. Additional examples of air ions include radicals such as Hydroxyl Radical (OH.).

The inventors have found that needle points, surprisingly, a plurality of them is the most simple, cost effective and energy efficient method of bipolar ionization. A high voltage alternating current (AC) or direct current (DC) source is applied to needles, which are a non-grounded conductive surface, causing them to build up a positive or negative change on that surface. If the surface has a sharp tip with near-zero surface area there will not be enough surface to hold the charge and the energy of the charge will be dissipated into the surrounding air to create ions.

The sanitizer 30 including the ion generator 60 having a controller 64 and electrodes 70 is generally fit within a housing 32 having a cover 50 and a backplate or base 40. The housing 32 is generally meant to protect the interior components and provide a pleasing look and feel to the sanitizer. Of course, the housing 32 may be made in any size, shape, style, or configuration and in some embodiments, such as to blend in with the surrounding style or decor. The base 40 of the housing 32 may also be configured in any size, shape, or configuration and may be formed to fit to or attach to a variety of surfaces 10 including contoured surfaces. The base 40 is generally used to mount the sanitizer 30 to another surface 10 such as a door, wall, fixture, or proximate to any other surface or fixture requiring sanitization. Of course, it is possible to mount the sanitizer 30 out of sight yet proximate to the surface to be sanitized without requiring certain portions of the housing 32. In addition, the base 40 may be configured to retain a variety of different sizes, shapes, and configurations of the ion generator.

As illustrated in the Figures, the sanitizer 30 may include a lens 34 or an opening on the housing 32 which allows motion to be sensed, initiating the process of sanitizing. For example, if the sanitizer 30 is placed on a wall, the approach of a person and placing the hands under the outlets may activate the sanitizer 30. The sanitizer 30 may provide a visual or audible feedback when activated, such as through illumination of a green light or other mechanism. The sanitizer 30 may include a visual or audible warning when function is impaired or the battery life is near the end of its life. In addition, a light pipe, such as a ring in the sanitizer 30 may provide an indicator of proper function, such as a blue or green diode directed through the light pipe. To save energy, the diode may be pulsed, yet to a person viewing it, it looks constantly on. Instead of photo cell sensors or motion detectors, the controller may include a simple switch or a tab to be pressed by users to activate the sanitizer 30. An accelerometer can detect motion when sanitizing items other than hands, such as door handles, appliance surfaces and the like, and other types of fixtures as well and an accelerometer causes less battery drain than a motion detector or photo cell. For example, upon swinging open the door when someone enters a restroom, the accelerometer would be triggered which would cause the sanitizer 30 to activate for a specified time period. Therefore, when the person leaves the restroom, the door handle has been sufficiently sanitized, and typically has had sufficient time to dry from any residual liquid from the sanitizer 30. In addition, the opening of the door upon exiting the restroom would also trigger the accelerometer and activation of the sanitizer 30 sanitizing the door handle after the person leaves. Because the sanitizer 30 only functions during use of the restroom, specifically motion of the door, battery life is conserved.

FIG. 1 illustrates a door on which an exemplary sanitizer 30 is placed to sanitize a fixture 20 such as the illustrated door handle. The illustrated sanitizer 30 as further provided in FIG. 6 includes a fluid reservoir to enhance the ions and generated chemicals interacting with the surface to be sanitized. As the electrodes emit cold plasma, the electrical field may be used to move the ions and sufficiently sanitize the fixture without the use of fans, $CO_2$ cartridges and the like, and the liquid from the fluid reservoir increases the amount of ions as well as creates chemicals and compounds such as hydrogen peroxide that are sufficient sanitizers.

The Figures illustrate a sanitizer 30 that uses a high frequency AC current applied to the electrode 70 containing the ion sources 82, which is also herein referred to as the ion electrode 80. The ion sources 82 are illustrated as small points 84 but could be carbon fiber brushes or the like which include many tips, each acting as an ion source in place of the points. In the sanitizer 30 that includes an ion electrode having an applied AC current, a second electrode also may be referred to as the reference or ground electrode 90 is included and spaced some distance apart from the ion electrode 80 to prevent generation of ozone or arcing. As described in more detail later, as the AC current is applied to the ion electrode 80 with 1-80 $H_z$, preferably a 5-70 $H_z$, more preferably 10-60 $H_z$ of alternating current, the ion electrode is in turn driven by a transformer cycling at a high frequency, such as 20-400 $kH_z$ on and off in either the positive or negative direction, typically in the higher end of the range. The ions, both positive and negative, leave the tips of the ion sources 82 on the ion electrode 80 and are pulsed outward until they cover the desired surface. Of course, they may be assisted by other methods, such as compressed gas, fans, or the like. In addition, in some embodiments, the ions emitted from the ion sources 82 may be drawn to the ground electrode 90 which helps them in the design, illustrated in FIG. 9, move across the hands or fixture located between the two electrodes specifically, the ion electrode 80 to the ground electrode 90. The high frequency AC sanitizer 30 generally has a voltage of 4,000-75,000V, preferably 6,000V, when voltage is measured by the root mean square (RMS) method. The current output is typically 0.0002 amps and input will vary with the power source, typically 40-200 milliamps for most batteries. The input voltage may vary but is expected to be between 9-24V DC although 6-40V may be common.

Figure 6:
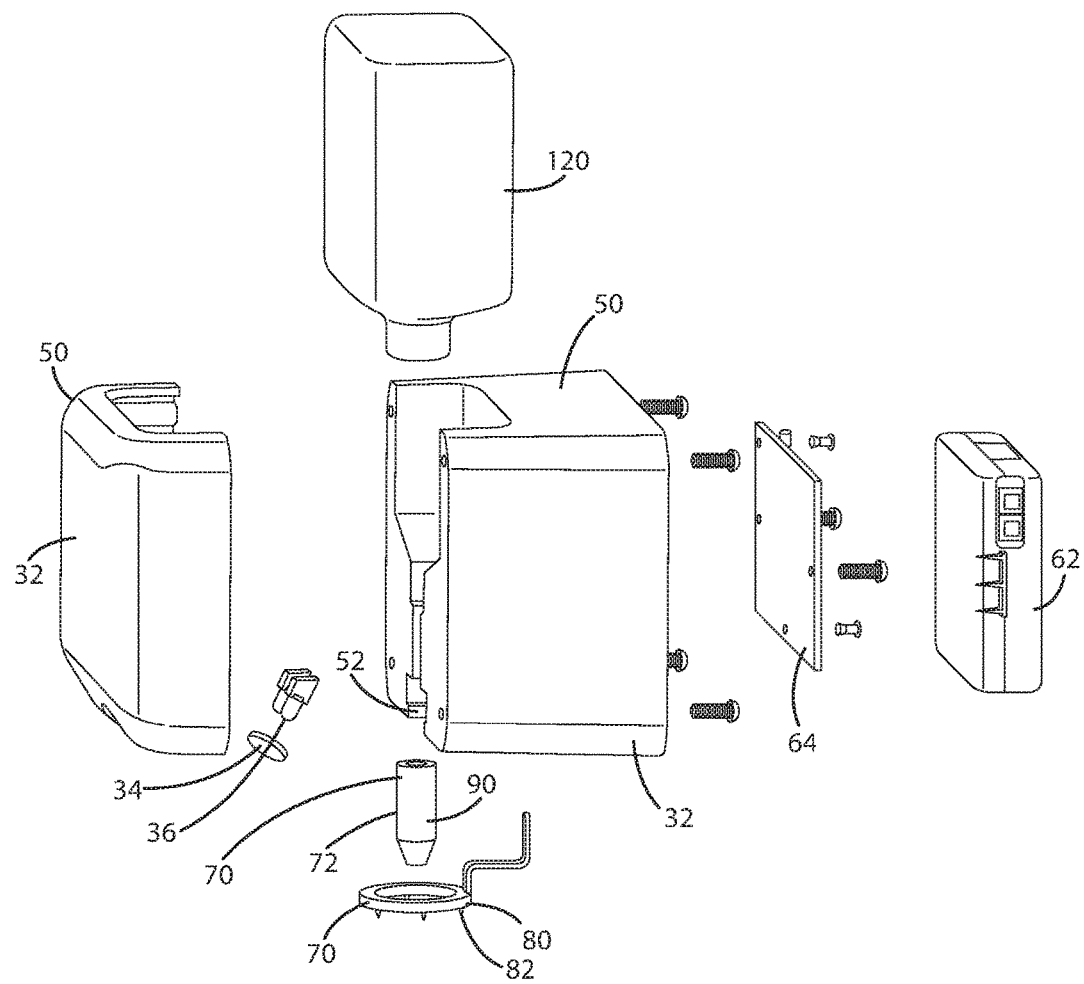
FIG. 6 is a front exploded perspective view of the sanitizer in FIG. 1.
Figure 9:
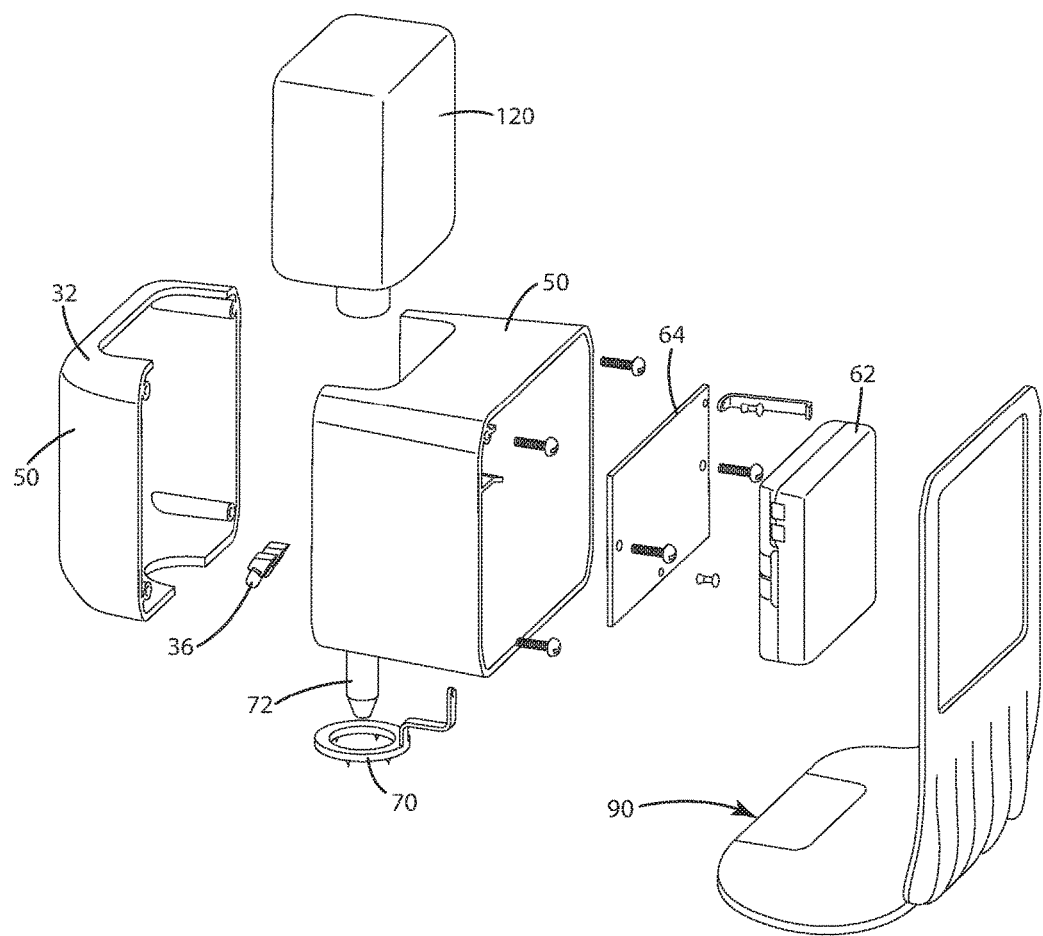
FIG. 9 is an exploded rear perspective view of a sanitizer in FIG. 8.

As further illustrated in FIGS. 6 and 9, the sanitizer 30 generally includes a base 40 in which the sanitizing apparatus, including a battery 62, controller 64, and electrodes 80, 90, is secured and a cover 50 placed over such components and secured to the base 40. The base 40 may include cavities for a battery compartment 54 and a controller cavity 56 as well as other cavities for receiving electrodes 80, 90, such as the illustrated electrode cavities 58. The electrodes 80, 90 are connected to the controller 64 with connectors or electrical leads.

The sanitizer 30 may include two ion electrodes 80 and eliminate the reference or ground electrode. The use of two ion electrodes 80, each including ion sources 82, has a sanitizing apparatus that uses a pulsed DC of typically 3,000-7,500 volts typically 6,000 volts is applied to each electrode 80 with, for example, one of the electrodes 80 emitting positive ions while the opposing electrode 80 emits negative ions. As such, the ions are drawn across the gap and any object in such a gap, between the two ion electrodes 80 as the electrical field propels the ions toward the opposing electrode 80. A microprocessor controls the pulsed DC.

The pulsed DC voltage may, for example, be produced by controlling a pair of transistors separately with pulse width (PWM) modulated signals from separate outputs of the microprocessor. Each transistor is used to energize the primary coil of a flyback transformer (e.g. one transformer and flyback transformer for the positive electrode and one transformer and flyback transformer for the negative electrode). When the transformer is switched off by the PWM signal from the microprocessor, the current in the primary coil and the magnetic flux drops. The voltage in the secondary coil becomes positive and current can then flow from the flyback transformer and create a voltage output at the electrode 80.

Figure 3:
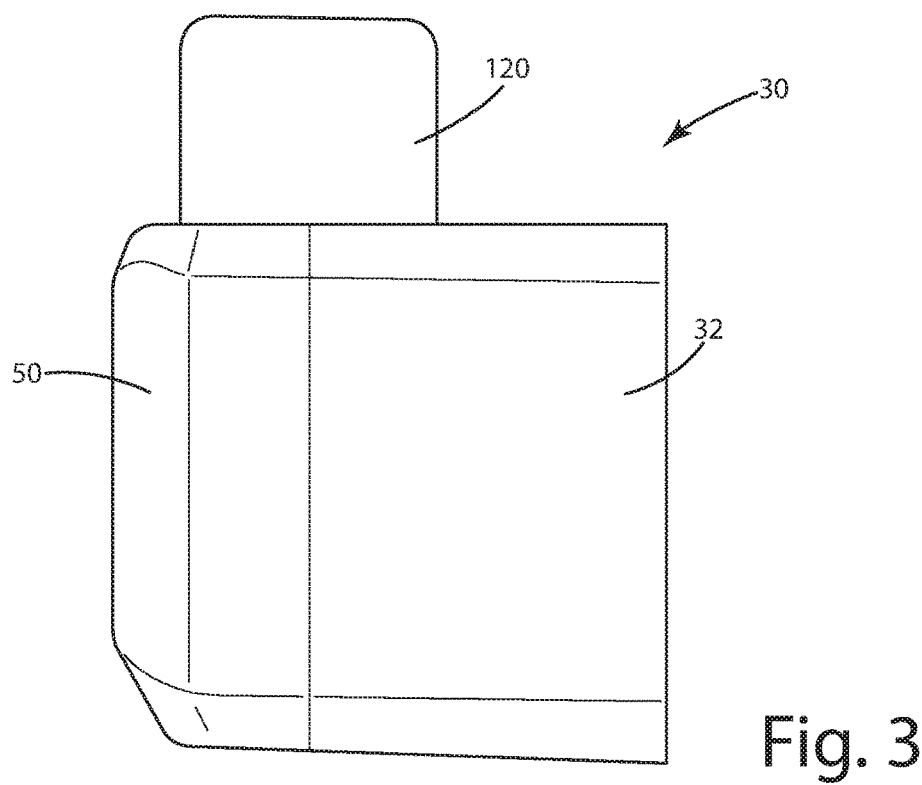
FIG. 3 is a right side view of the sanitizer in FIG. 1.

One electrode 80 of the sanitizer 30 of FIG. 3 may be connected to the secondaries of both flyback transformers so that a single electrode 80 produces both positive and negative ions from an AC output and the other electrode 80 may function as a ground. As shown in FIG. 34, a first drive signal 100 or PWM pulse train which will be described in more detail below drives the first flyback transformer to create the positive half of the AC output. Likewise, a second drive signal 102 or PWM pulse train drives the negative half of the AC output 104. The inventors have discovered that a "Dead Zone" 106 or period of time where both PWM pulse trains (i.e. first drive signal and second drive signal) are turned off is useful for efficient operation. Without a dead zone 106, the output from the flyback transformer driven by the first drive signal 100 may "shoot through" the flyback transformer circuit driven by the second drive signal 102 and vice versa. This may cause the outputs from each flyback transformer to somewhat cancel each other out. Adding a correctly sized dead zone 106 was shown to double the operating efficiency of the circuit. In other words, the voltage of the AC output 106 doubled while using the same amount of power.

Additionally, the level of ionization was found to increase significantly with the addition of a "Dead Zone" 106. It is thought that an abbacy change at a sharp discharge point 84 (needle point) causes emitted positive ions to combine and neutralize some of the negative ions that were emitted in the previous cycle and vice versa.

For electrical efficiency, the dead zone 106 must be a long enough time period for the previous half cycle output of the transformers energy to be dissipated and reach zero volts. The amount of energy that is initially stored in the flyback transformer by a $t_{on}$ pulse 108 shown in FIG. 34 and the transformer circuits characteristics (inductance, DC resistance and capacitance) determine the required duration of the dead zone 106. In one example, the dead zone 106 should be no less than 2 microseconds and no more than 20 microseconds.

For ion generating efficiency, the duration of the dead zone 106 is longer that what is required for electrical efficiency. The duration of the dead zone 106 for optimum ion generating efficiency also depends on the velocity of the air passing by the discharge point(s) 84. If the air is still (velocity=0) then a large dead zone 106 is required. If the velocity of the air passing over the discharge point(s) 84 is great, a smaller dead zone is required. The inventors have found a dead zone 106 of 50-100 ms is optimal. With high velocity air such as a high speed hand dryer (185 MPH) or the $CO_2$ powered door handle sanitizer smaller dead zone of 2-10 ms is optimal.

The first drive signal 100 is a pulse width modulated, PWM drive signal from the microprocessor to a circuit that produces the positive half of the AC output 104. The first drive signal 100 will be active while the second drive signal 102 is off. The first drive signal 100 is operated at a frequency between 20 KHz to 400 KHz depending on the characteristics of the flyback transformer being used. Ideally, a small flyback transformer with very low primary DC resistance and very low inductance is more energy and cost efficient and can be driven at a higher frequency. However, it has been found that the circuit works well with larger flyback transformers at the lower frequency range shown. The second drive signal 102 is similar to the first drive signal, except it drives the negative half cycle of the AC output 104.

The high voltage AC output 104 is shown in FIG. 34 as it relates to the two drive signals 100, 102 and the dead zone 106. Although, the AC output 106 is shown with a peak voltage of 6 KV, this can be varied from 2.5 KV to 12 KV by changing the PWM of the first drive signal 100 and the second drive signal 102.

The period of the drive signals 102, 104 is T. The period, T is inversely proportional to the frequency, f (T=1/f). The duty cycle is defined as the relationship between on time ($t_{on}$) and off time ($t_{off}$) during one period (T). Because flyback transformers operating in discontinuous mode, (i.e. the current in the secondary of each flyback transformer is allowed to discharge completely to zero) the duty cycle should be less than 50%—meaning that off time is greater than on time. Typically, the duty cycle approaches 50% to achieve maximum voltage output. However, the inventors unexpectedly discovered that it is not necessary and even detrimental for the duty cycle to approach 50%. This is because it is necessary to utilize sufficient off time for the transformer circuit (transformer and voltage multiplier) to fully discharge before applying another pulse. In one example, it was discovered that a duty cycle of 10% resulted in maximum AC output 104 voltage. The duty cycle may be reduced as low as 2% to adjust the AC output 104 to its minimum.

The first drive signal 100 and second drive 102 signal may also be comprised of signals having different duty cycles. For example, if the duty cycle for the first drive signal 100 is 20% and the duty cycle for the second drive signal 102 is 30% a balance of more negative ions than positive ions may be achieved, which is beneficial for human wellness. Also, in an indoor environment with lower air quality, more negative ions may get "used up" and therefore, the negative ion output may need to be increased further compared to the positive ion output. In another example, if the air is passing through a duct that has a negative surface charge, (static electricity) more positive ions may need to be created as compared to the amount of negative ions being produced.

Of course, the electrodes 80, 90 as well as the sanitizer 30 may be made in a variety of other configurations such that the electrodes 80, 90 may surround entry doors, restroom doors, kitchen doors, faucets, keypads, hospital fixtures, or any device that is touched or is near to a device that is touched on a regular basis. Therefore, in addition to hands, the device may sanitize from surfaces, bacteria or other pathogens, which are undesirable. In addition, electrodes 80, 90 can be built into various phone and tablet or computer cases, such as those used by doctors and hospitals to prevent the spread of infectious diseases. The sanitizer 30 may also be used proximate to other items receiving high frequency of touches such as vending machines, shopping carts, card readers, credit card payment devices and any other devices, where a person desires to sanitize their hands.

The illustrated sanitizing apparatus generally includes a battery 62 and a control circuit such as the illustrated controller 64. The electrodes 80, 90, as illustrated, are formed of a conductive plastic material such as a conductive ABS material but of course could be formed of other conductive plastics such as a conductive polycarbonate or a blend of ABS and polycarbonate. In addition, the electrode 80, 90 could be formed of metal including stainless steel, aluminum, nickel or other metals and metal alloys. Forming the electrodes 80, 90 of a plastic material allows molding of electrodes including, as illustrated in the Figures, molding the electrodes in place directly to the circuit board, specifically the controller 64. The present invention uses a conductive ABS material that has been doped with carbon but also could be doped with other materials, such as 15% stainless steel. Use of a conductive ABS allows a cost-effective material that is flexible and easy to assemble. Other cost-effective conductive polymers include conductive polypropylene, doped with carbon, boron, or the like. In addition, using a conductive plastic avoids potential corrosion of metal electrodes and many of the harsh environments where sanitizers 30 are desirable to be placed. For example, in a restroom, humidity as well as harsh cleaning supplies are regularly applied or incurred by fixtures, including the sanitizer 30 within the restroom and after a certain time period, even stainless steel may corrode.

The housing 32, including the base 40 and cover 50 is generally formed from a non-conductive material to prevent the cover 50 from being electrically conductive with the electrodes. Of course, the housing 32 may be formed from metal or other materials if the electrodes are insulated from the housing 32. The electrodes are injection molded, although other methods may be used. To obtain the points 84, as illustrated in FIGS. 10-12, which is not possible with injection molding, given the size of the points 84, the dies are scored to create flash at the points, which creates the pointed surface the present invention uses to create the ions. The illustrated points 84 protrude about 4 mm from the electrode base 40, which is illustrated as about 4 mm wide and 1.6 mm thick, although other dimensions could be substituted. The points 84 of the electrode 80, forming the ion sources 82, are recessed in the sanitizer 30 to avoid contact with humans. In the present invention, the ion sources 82 are generally spaced more than a ¼" or 6 mm apart, but less than 2" or 50 mm apart. It has been found that the pulse effect to drive the ions away from the ion sources 82 at less than ¼" apart generally causes the ions to cancel each other out and at more than 2" apart, the ions may not be applied as uniformly to the surface 10. In the illustrated embodiment, the ion sources 82 are spaced about ½" or about 12.5 mm apart. The most effective range of spacing has been found to be about ⅜" to 1".

The sanitizer 30 may be attached to a desired area through a variety of mechanisms, such as the illustrated fasteners 42.

As assembled, it is desirable for the sanitizing apparatus to be unobtrusive and maintenance free as possible. Of course, as described above, the sanitizer 30 may be attached maybe directly into the fixture 20, appliance, or other surfaces 10.

Figure 4:
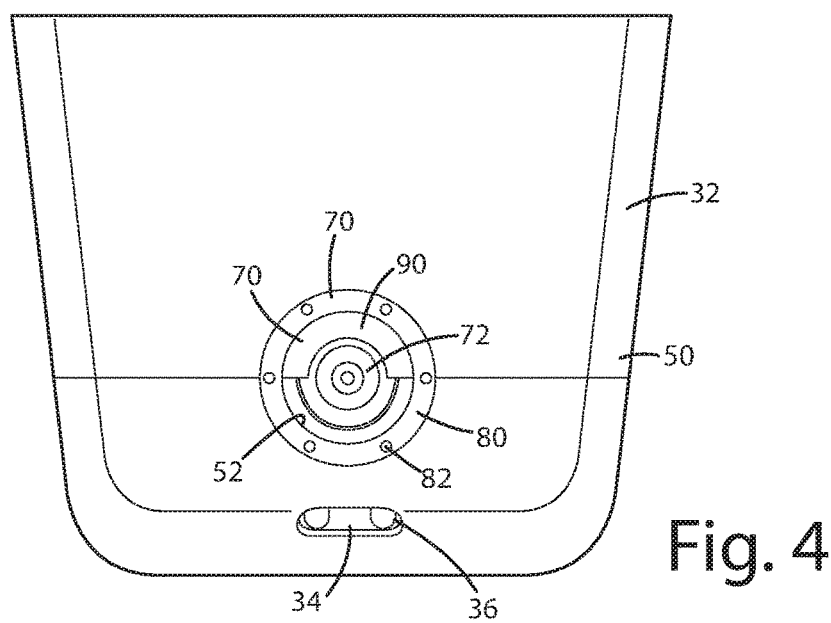
FIG. 4 is bottom view of the sanitizer in FIG. 1.
Figure 7:
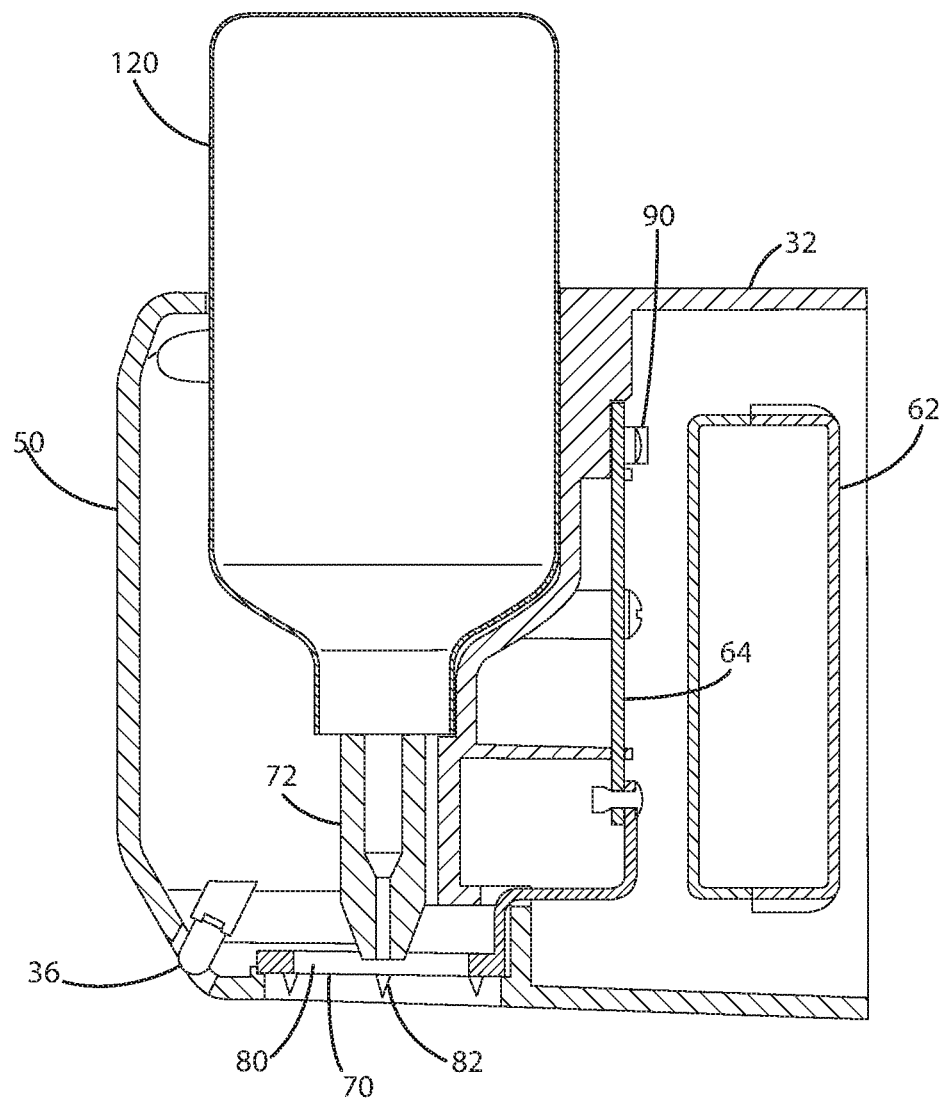
FIG. 7 is a sectional view of the sanitizer in FIG. 1 along lines 7-7.

The sanitizer 30 as illustrated in the Figures is specifically configured to provide a wide dispersal of ions particularly with the force of the liquid such that the hands or fixture does not need to be centered between two electrodes. The illustrated sanitizer 30 may have a wide dispersal of ions 360° of ion sources but of course, by removal of some of the ion sources from the ion electrode, the coverage of ions may be reduced. In addition, the number of ion sources 82 shown on each ion electrode 70 may vary as well as the position or placement may vary depending upon the desired application. It has been found that use of the present sanitizer 30 may provide sufficient generation and dispersal of ions across a six-foot radius area from the sanitizer 30 to substantially sanitize the surfaces or at least reduce the number of pathogens and other infectious diseases on such surfaces. For example, a restroom, kitchen, or other facility may include a number of these sanitizers secured to ceilings, countertops, or walls, thereby providing substantially continuous coverage across the whole area to sanitize or reduce the number of infectious diseases on a majority of the proximate surfaces. The liquid tank when combined with the ionizer provides additional sanitizing capabilities, including producing certain sanitizing chemicals that are not subject to the quick recombination of the normally produced ions. The illustrated sanitizer 30 in FIGS. 8 and 9 includes a ground electrode 90 and as such, uses a high frequency transformer to drive an AC current applied to the ion electrode to generate the ions at the ion sources 82. Of course, a pulsed DC version where the ground electrode 90 is swapped for an ion electrode 80 may also be used, but preferably would be placed in a setting experiencing air movement, or where a user would place their hands or object within a set proximity. Similar to the above, the electrodes 80, 90 also may be formed of a conductive plastic material such as a conductive ABS, although again, various other metals or alloys may also be used to create the electrodes 80, 90. The electrodes each include connectors allowing for easy assembly to the controller. Of course, the configuration of the sanitizer 30 and individual components therein may vary depending upon the desired application. The controller 64 is expected to be sealed with epoxy or another material. The battery 62 as used in the sanitizer 30 may be any type of battery 62, however a long-life battery such as a lithium ion battery is generally preferred. The use of a lithium ion battery allows extension of the intervals between required maintenances and replacement of the battery, as compared to more traditional batteries. Of course, the sanitizer 30 may be hardwired into the building power supply. The illustrated sanitizer 30 may be assembled through a variety of methods including where the cover 50 is capable of being split into multiple pieces and snapped together or ultrasonically welded together with the electrodes fitting within grooves on the cover 50. In addition, the ion electrode 80 and ground electrode 90 may be formed with a small split on at least one side allowing expansion of the electrodes 70 as they slide over the cover 50 and then contraction as they fit within the specified and desired groove. However, as illustrated in FIGS. 4, 6 and 7, the ion electrode 80 may be loosely placed inside the cover 50 near the opening 51.

Figure 20:
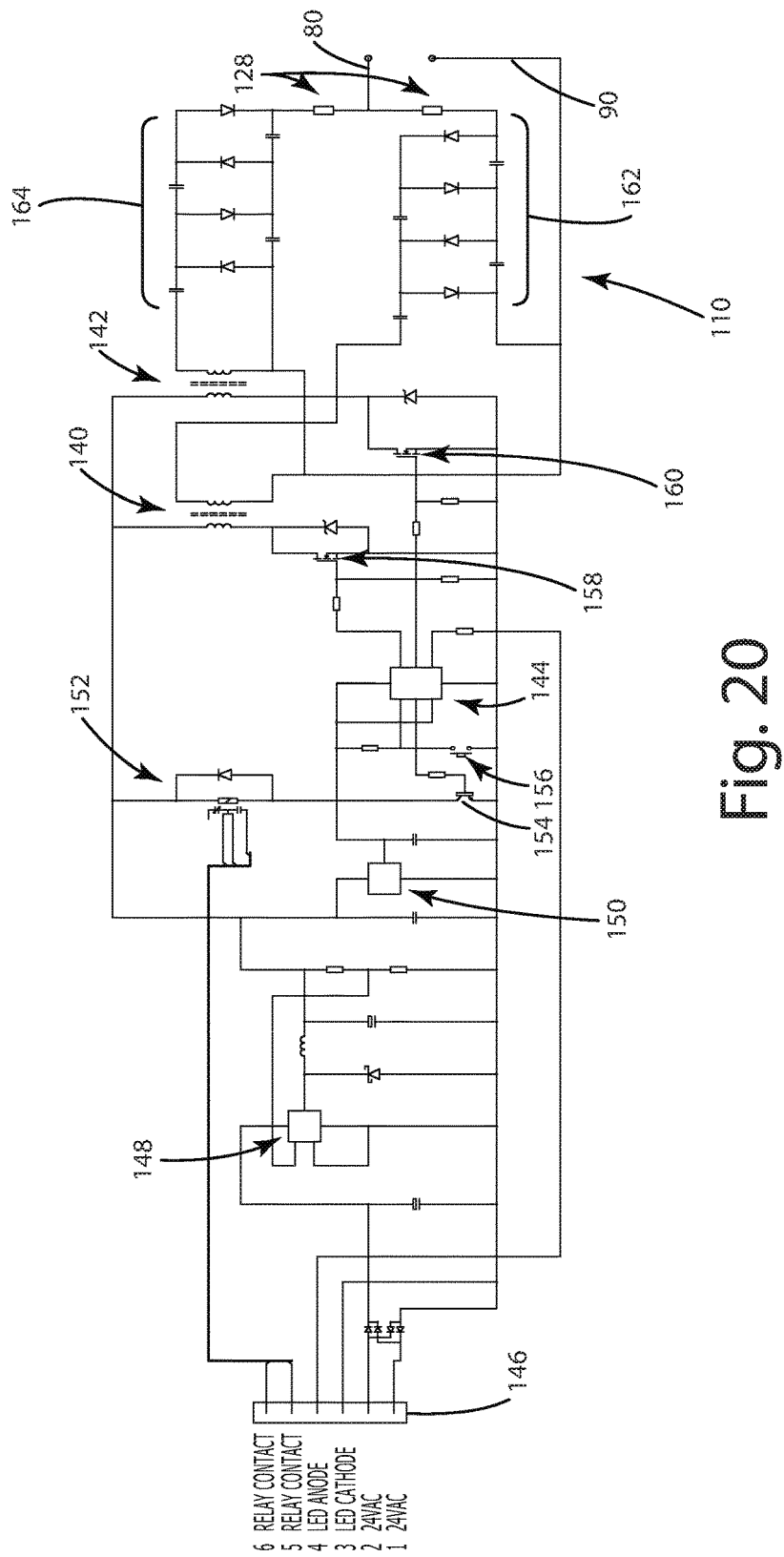
FIG. 20 is a schematic diagram of an alternative ion generator using two flyback transformers.

As shown in FIG. 20, an additional ion generator 110 includes a circuit assembly for ion generation. The circuit assembly includes a wiring connector 146 having a pair of relay terminals, a light emitting diode (LED) anode terminal, an LED cathode terminal, a 24 VAC positive terminal, and a 24 VAC negative terminal (ground). The LED cathode terminal is connected directly to the 24 VAC negative terminal.

A switching regulator 148 having an output is electrically connected to the 24 VAC positive terminal and the 24 VAC negative terminal of the wiring connector 146. An input capacitor is connected across the 24 VAC positive terminal and the 24 VAC negative terminal to prevent large voltage transients input to the switching regulator 148 from the 24 VAC terminals. The switching regulator 148 outputs a lower voltage on the output connected to the 24 VAC negative terminal (ground) through a Schottky diode and connected to an inductor which is also connected to an output capacitor tied to the 24 VAC negative terminal. The Schottky diode provides a return path for the inductor current when the switching regulator is deactivated. Two resistors are connected in parallel to the output capacitor and a feedback line is connected between the output resistors and to the switching regulator. Although, the switching regulator 148 of the currently discussed ion generator 110 is a LM2576 manufactured by ON Semiconductor, it should be understood that other ion generators 110 may use different switching regulators 148, or may not use a switching regulator 148 at all.

A positive voltage regulator 150 having an output is connected to the output resistors of the switching regulator 148 and to the 24 VAC negative terminal for regulating the voltage of the output from the switching regulator 148. A capacitor is connected in parallel with the resistors. An additional capacitor is connected between the output of the positive voltage regulator 148 and the 24 VAC negative terminal (ground). The voltage regulator 150 of the currently discussed ion generator 110 is an L78L05 manufactured by ST Microelectronics, as with the switching regulator 148, it should be understood that other ion generators may use different positive voltage regulators 150, or may not use a positive voltage regulator 150 at all.

A relay 152 having a coil is electrically connected to the relay terminals of the wiring connector 146 and to the output of the switching regulator 148. A reverse biased diode is connected across the coil of the relay 152 to allow transient voltages generated when the voltage is removed from the coil to be dissipated in the resistance of the coil wiring. The relay 152 of this ion generator 110 is a G5V-1 manufactured by Omron, it should be appreciated that other relays 152 may be used and that other ion generators may use relays 152 with different characteristics, or may not use a relay 152 at all.

A microprocessor 144 having a plurality of input/output (I/O) terminals is connected to and powered by the output of the switching regulator 148. A bipolar transistor 154 having a gate input is connected to the coil of the relay 152 which is also tied to the to the output of the switching regulator 148. The bipolar transistor 154 is also connected to ground (24 VAC negative terminal). The gate input of the bipolar transistor 154 is connected through a resistor to one of the I/O terminals of the microprocessor 144. The microprocessor 144 can energize the coil of the relay 152 through the I/O terminal connected to the gate input of the bipolar transistor 154. Another I/O terminal of the microprocessor 144 is connected through a resistor to the LED anode terminal of the wiring connector to control an LED. A separate I/O input is connected to the output of the switching regulator 148 through a resistor and tied to ground by a switch 156. Two other I/O terminals of the microprocessor 144 include a first pulse width modulated (PWM) output and a second PWM output. The microprocessor 144 utilized for the currently discussed ion generator 110 is a PIC12F609 manufactured by Microchip, however, it should be understood that other microprocessors 144 may be substituted.

Figure 21:
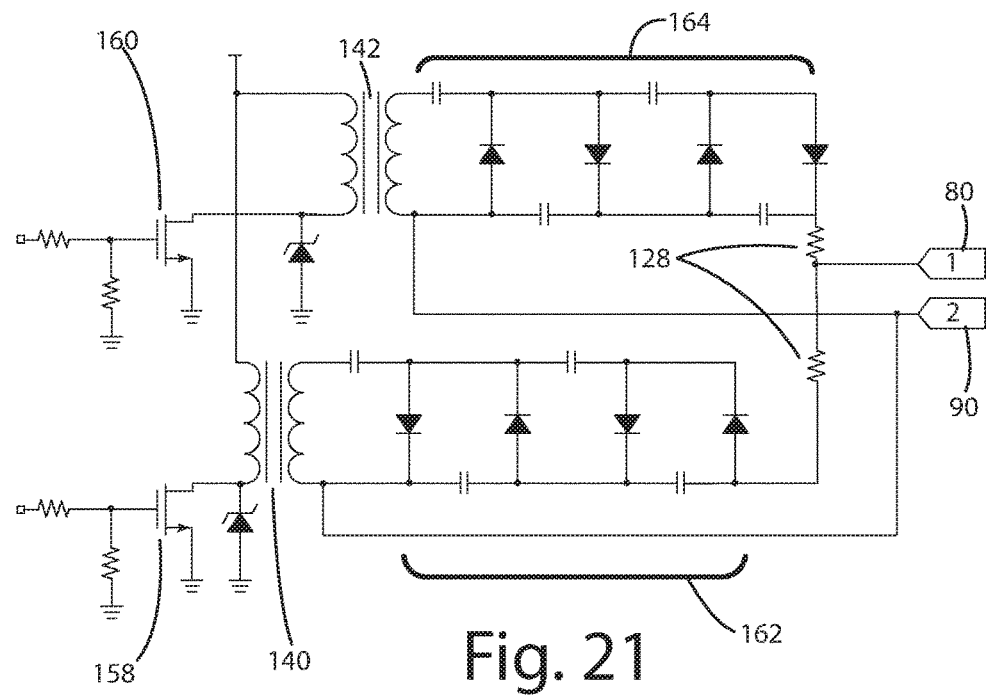
FIG. 21 is a partial schematic diagram of the ion generator shown in FIG. 18.

As shown in FIGS. 20 and 21, the first PWM output of the microprocessor 144 is connected to a first switching transistor 158 through a series resistor and a resistor connected to ground. A Schottky diode is connected across the first switching transistor 158 for preventing any overvoltage across the first switching transistor 158. In a similar fashion, the second PWM output of the microprocessor 144 is connected to a second switching transistor 160 through a series resistor and a resistor connected to ground. A Schottky diode is connected across the second switching transistor 160 for preventing any overvoltage across the second switching transistor 160.

A first flyback transformer 140 having a primary winding and a secondary winding is connected to the first switching transistor 158. More specifically, the primary winding of the first flyback transformer 140 is connected to output of the positive voltage regulator 150 and to the 24 VAC negative terminal (ground) through the first switching transistor 158. Thus, the first switching transistor 158 can control the amount of current through the primary winding of the first flyback transformer 140 in response to the first PWM output of the microcontroller or microprocessor 144.

A second flyback transformer 142 having a primary winding and a secondary winding is connected to the second switching transistor 160. Specifically, the primary winding of the first flyback transformer 142 is connected to output of the positive voltage regulator 150 and to the 24 VAC negative terminal (ground) through the second switching transistor 160. Therefore, the second switching transistor 160 can control the amount of current through the primary winding of the second flyback transformer 142 in response to the second PWM output of the microcontroller 144.

Each flyback transformer 140, 142 in the circuit assembly is controlled by the PWM outputs to energize the primary coils of each flyback transformer 140, 142. When the switching transistors 158, 160 are switched off by the PWM outputs, the respective current and magnetic flux drops in the primary winding. The voltage in the secondary winding of each flyback transformer 140, 142 becomes positive, and current is allowed to flow from the transformer 140, 142, generating a high-voltage peak in the secondary winding.

A first output section 162 is electrically connected to the secondary winding of the first flyback transformer 140 for amplifying the high-voltage peak from the first flyback transformer 140. Similarly, a second output section 164 is electrically connected to the secondary winding of the second flyback transformer 142 for amplifying the high-voltage peak from the second flyback transformer 142. Each output section 162, 164 includes a multiplier bridge comprising a plurality of capacitors and diodes arranged in a ladder configuration. The secondary winding of the first flyback transformer 140 is also electrically connected to a reference terminal or ground 90.

Figure 22:
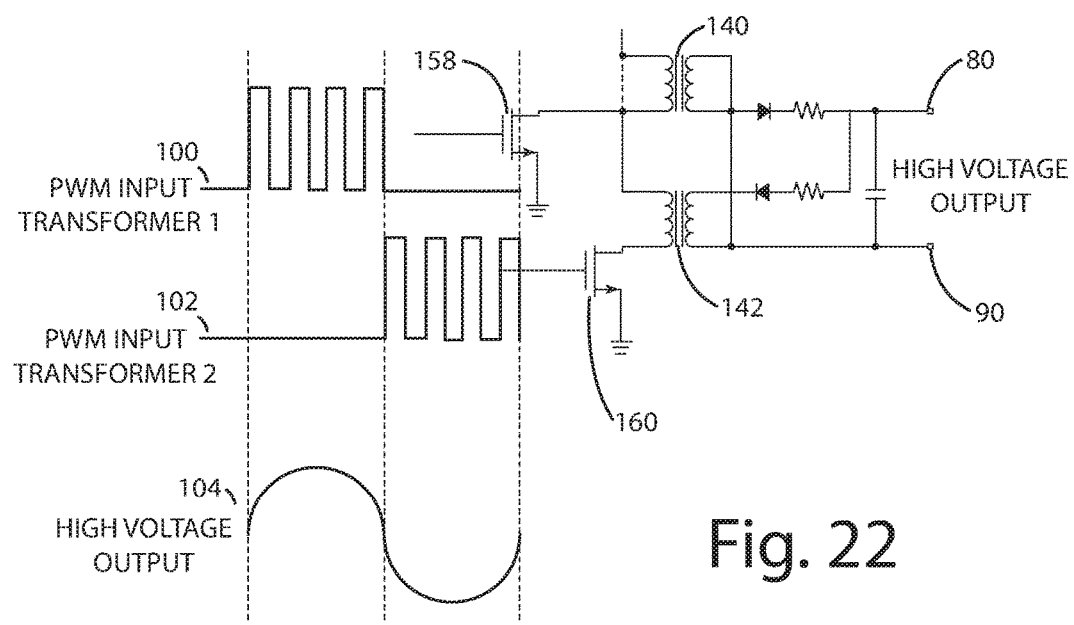
FIG. 22 is a schematic diagram of a simplified version of the ion generator shown in FIG. 18.
Figure 29:
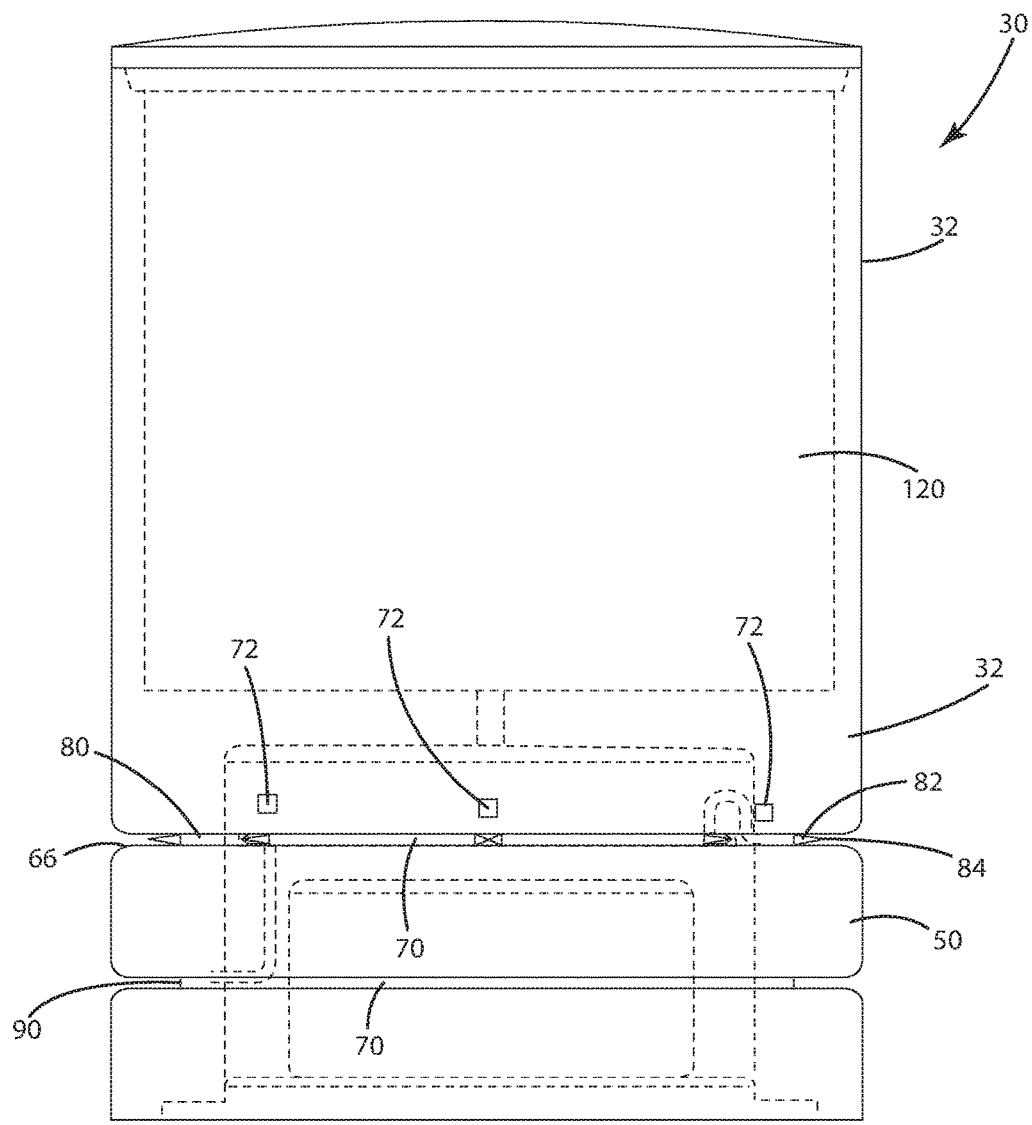
FIG. 29 illustrates a side view of an exemplary sanitizer.
Figures 30, 31:
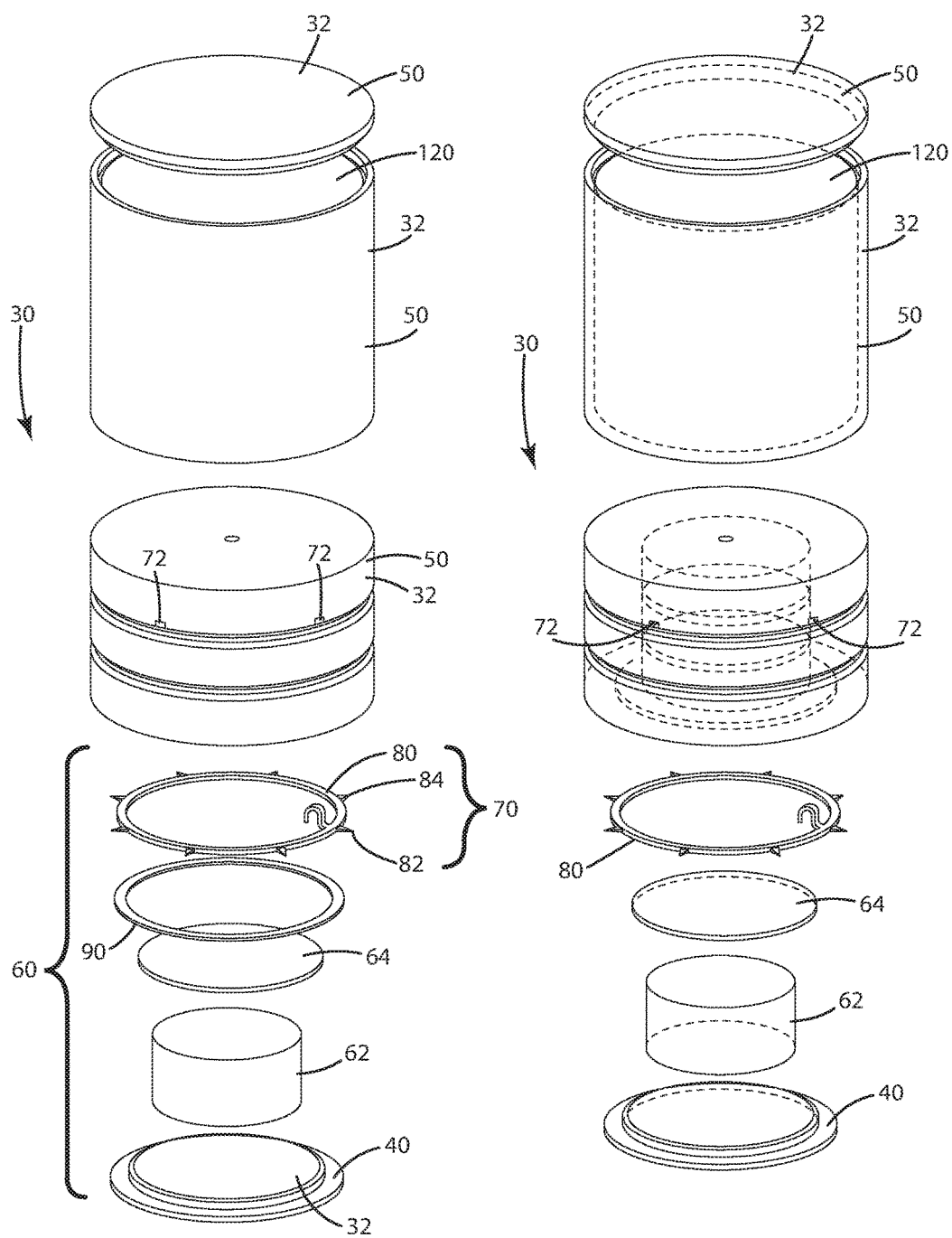
FIG. 30 illustrates an exploded side perspective view of the sanitizer in FIG. 29.
FIG. 31 illustrates an exploded side perspective view of the sanitizer in FIG. 29, with hidden passages showing liquid channels extending from the liquid reservoir to outlets proximate to the ion sources.
Figure 35:
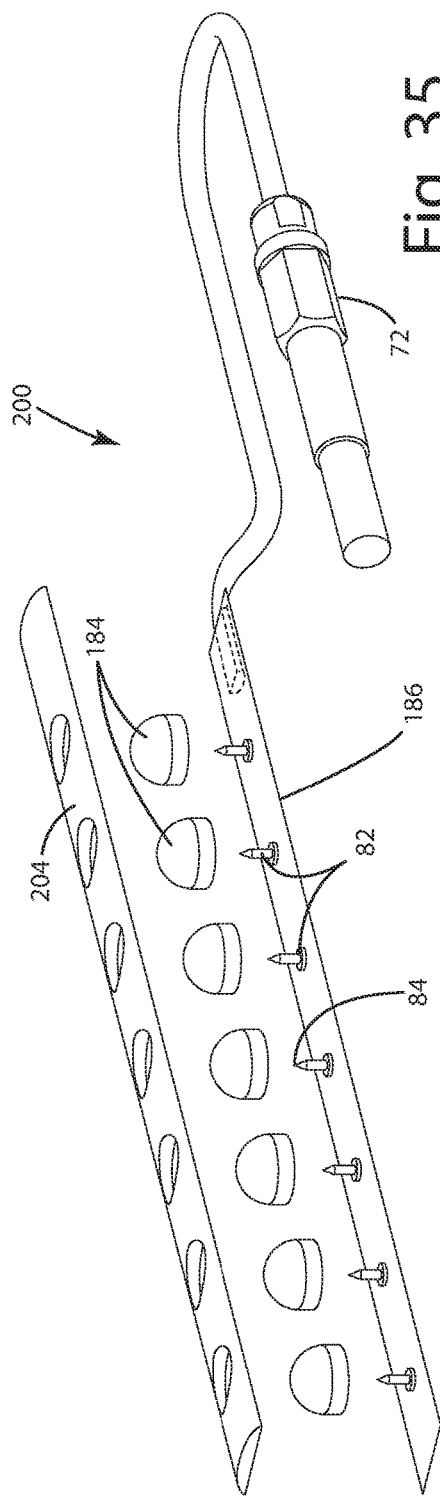
FIG. 35 is an exploded side perspective view of the ion electrode assembly in FIG. 32.
Figure 36:
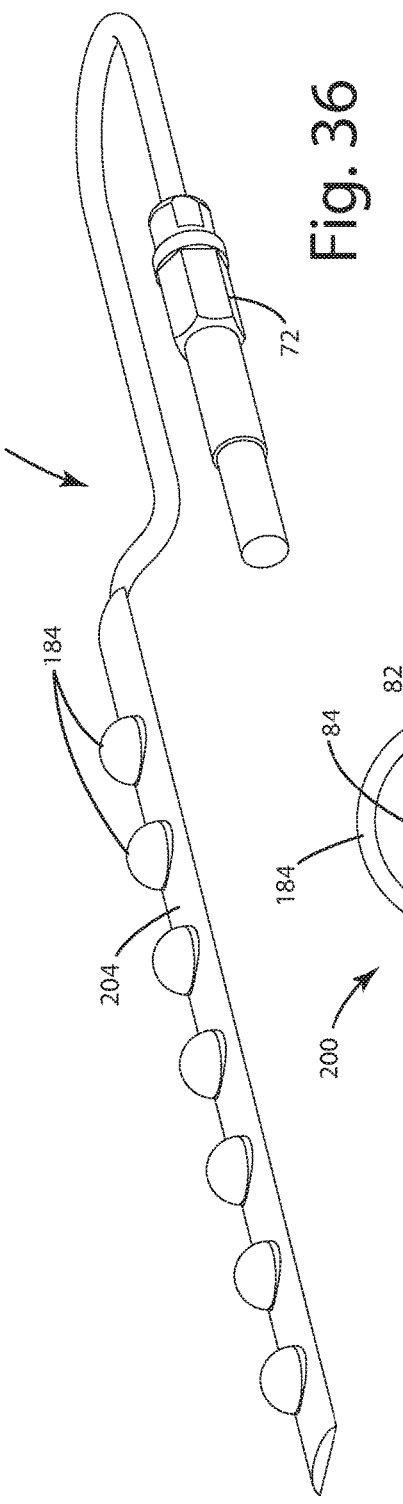
FIG. 36 is a side perspective view of the ion electrode assembly in FIG. 32.
Figure 37:
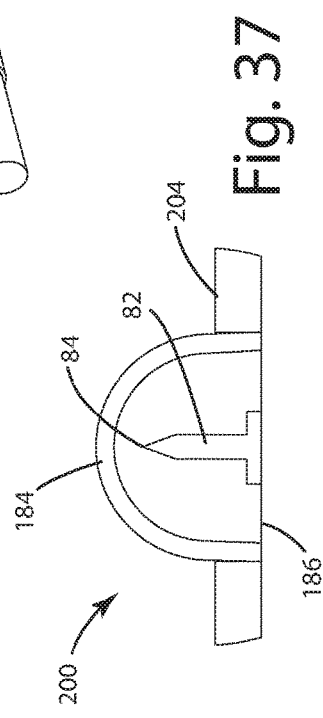
FIG. 37 is a cross sectional view of the ion electrode assembly in FIG. 32.
Figure 43:
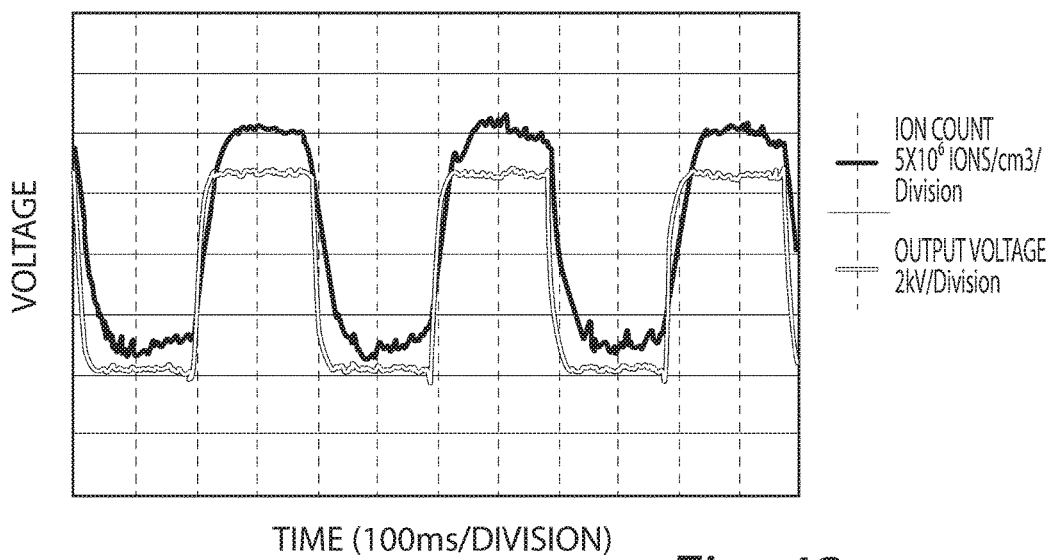
FIG. 43 illustrates the amount of ions produced by the new ion electrode assembly and new ion generator as well as the synthetic wave output in the ion generator.
Figure 44:
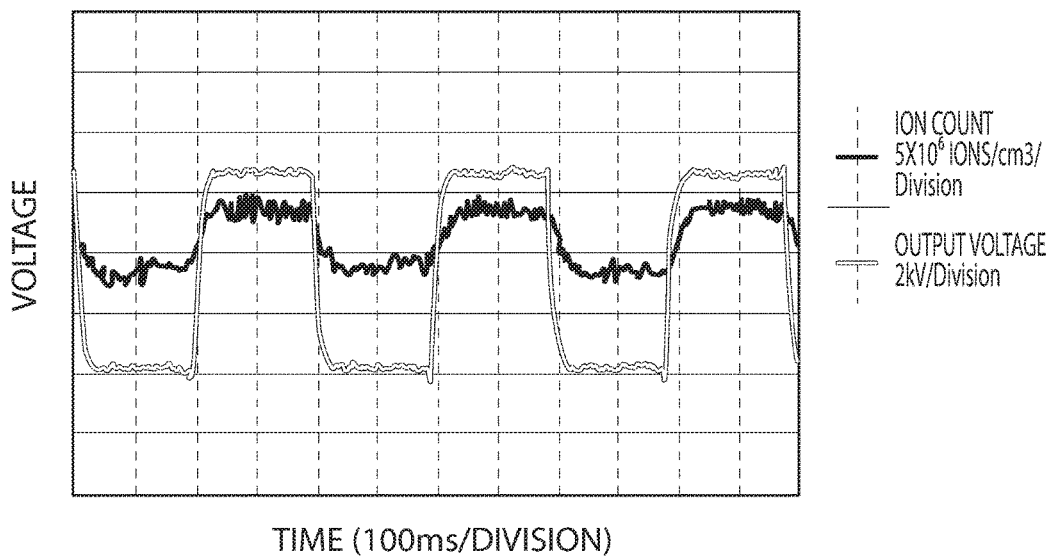
FIG. 44 illustrates the amount of ions produced by the new ion electrode assembly and new ion generator as well as the synthetic wave output in the ion generator.
Figure 46B:
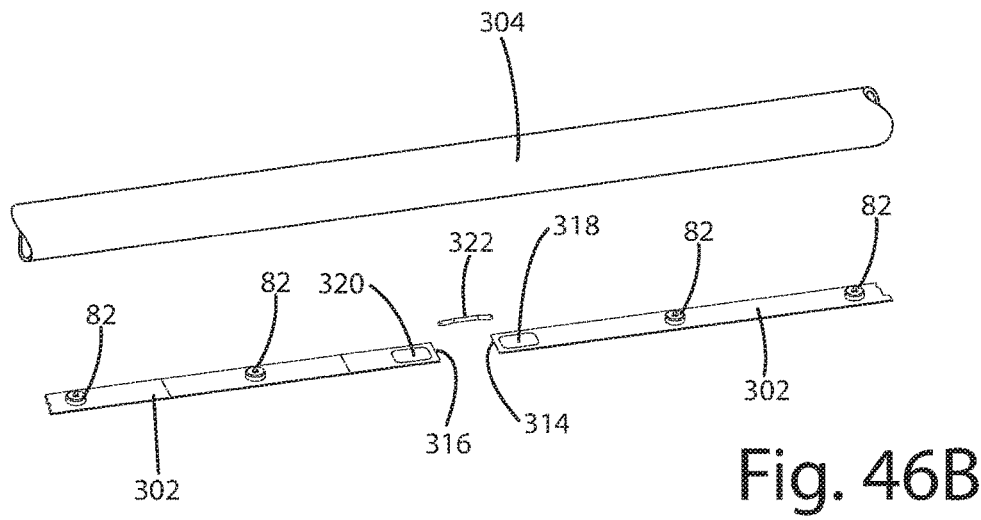
Figure 46C:
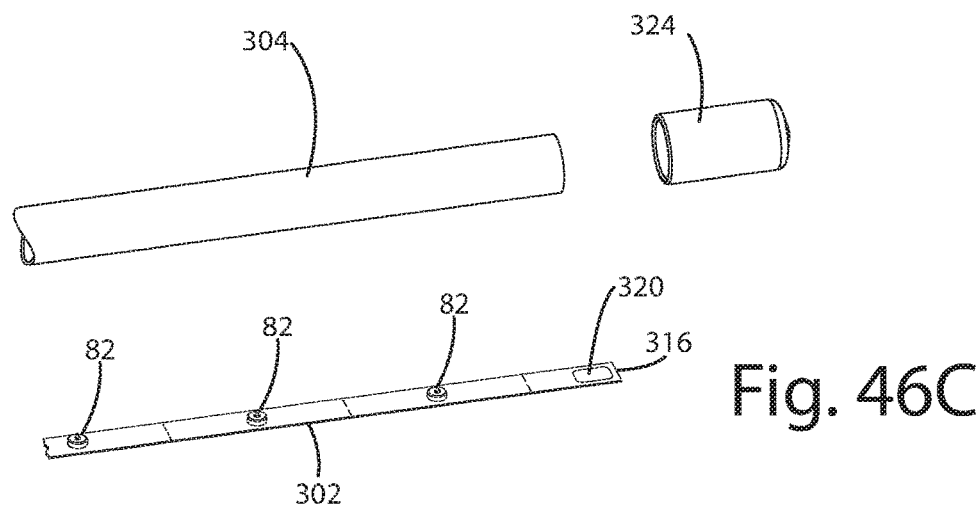

As illustrated in FIGS. 29 and 30, the sanitizer 30 may be formed in a puck shape with the ion electrode 80 in a groove 66 on a cover 50, and the ground electrode 90 in another groove 66. The grooves 66 on the cover 50 are spaced about 10-20 mm, preferably 10-15 mm, apart and the recesses forming the grooves 66 are about 14 mm deep, with the point 84 being recessed 3 mm from the surface. The electrodes 80, 90 are closer on the round design illustrated in FIG. 22 than the fork design because the electrodes 80, 90 being recessed avoids arcing that would otherwise occur if the electrodes were spaced less than 20 mm apart on the surface of the cover 50. Therefore, the groove 66 allows closer spacing of electrodes 80, 90 and a smaller package to the sanitizer 30. However, the depth of the groove relative to the spacing of the grooves 66 is also important as too deep of a groove 66 may prevent sufficient expulsion of the ions from the groove 66. As the electrodes 80, 90 are more recessed in the grooves 66, the spacing of the grooves 66 may shrink and as the electrodes 80, 90 approach the surface of the cover 50, the spacing of the grooves 66 increases to prevent arcing and ozone generation.

The battery 62 may also be rechargeable, and the sanitizer could include a USB port or other input that could provide charge to the battery 62. In addition, the device may include Bluetooth or Wi-Fi to allow control of the device with smartphones, computer, tablets, and the like, or for a person to check the status of all devices within a facility or within a given range. Control over the voltage output, and as such amount of ions generated as well as battery life could be controlled. Any inputs, such as a power supply input, USB input and the like may be covered to prevent liquid intrusion, such as if a sanitizer was used on a kitchen counter.

For use in a sanitizer, as illustrated in FIGS. 1-9, the ion generator of the sanitizer may be included as part of a fixture or appliance. One exemplary configuration is for the ion generating electrode with its points, brushes or other ion sources 82 to be located in a recessed area of the air channel or nozzle proximate to the exit and a metallic or conductive plastic ground plane ring near the exit or opening in the cover 50 or outer edge of the nozzle, or spaced below the opening allowing someone to place their hands between the ion electrode 80 and ground electrode 90. The ion electrode 80 and ground electrode 90 would be spaced as provided below or as illustrated. One benefit of reversing the ion electrode 80, particularly the ion sources 82, the sharp points of the ion sources are placed to minimize contact with hands and fingers. Of course, if the portions of the housing 32 or other features are metallic or formed from a conductive plastic, they may form the ground electrode (or in some embodiments to ion electrode) and the ion generating electrode 80 may be placed further in the channel or opening and electrically insulated from the nozzle/ground electrode. While the sanitizer 30 in the Figures illustrates a specific electrode 70 acting as the ground electrode 80 or ground plane, objects on the device or the sanitizer 30 could be formed as the ground plane. Generally speaking, the ground electrode may be placed anywhere so long as it is not too close to the discharge points 84 on the ion electrode, which could cause arcing and create ozone. Ozone is specifically not desired to create. The flexibility in placing the ground electrode is actually very surprising, especially that it makes little difference in the ions generated in the plasma field, but can be helpful in drawing the ions in a particular direction. One item of care is that the ground plane must be placed or configured to avoid creating a capacitive load. For example, to sanitize proximate to the kitchen sink or faucet, one of the sink or faucet could be a ground plane for the ion generating electrode. As it is a ground plane, and naturally grounded through the plumbing, the ion generator could be configured to attach the ground electrode to the metal pipes of the plumbing or metal fixtures of the plumbing. Therefore, the faucet is the ground, and a ring or plate could extend under the faucet or around the faucet, such as a plastic insert around the faucet and includes in a recess, the ion generating electrode. It is preferable to recess the ion generating electrode 80 to prevent contact with the ion sources 82 on the ion electrode 80 and to create a torturous pathway so minimize packaging around the ion electrode 80 and spacing required to the ground electrode 90.

It is important to note that the ion generator or sanitizer 30 generally includes a large resistor such as a 50 mega ohm protection resistor 128 in the present invention, which limits the current as a safety feature and limits it to micro amps of current. The ion generator could also be used in a shower to prevent growth of mold, bacteria and other pathogens in a shower, particularly public showers or enclosed showers where humidity stays present and promotes undesirable growth. Also, the more humidity that occurs in a shower the more effective the ion generator is at generating ions and therefore more effective at greater distances.

Figure 13:
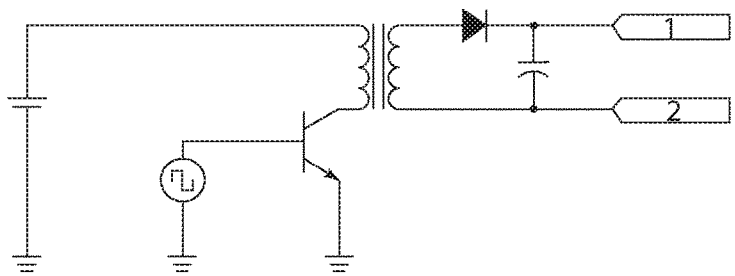
FIG. 13 is a schematic diagram of a high voltage DC bipolar ion generator, using positive and negative electrodes.
Figure 14:
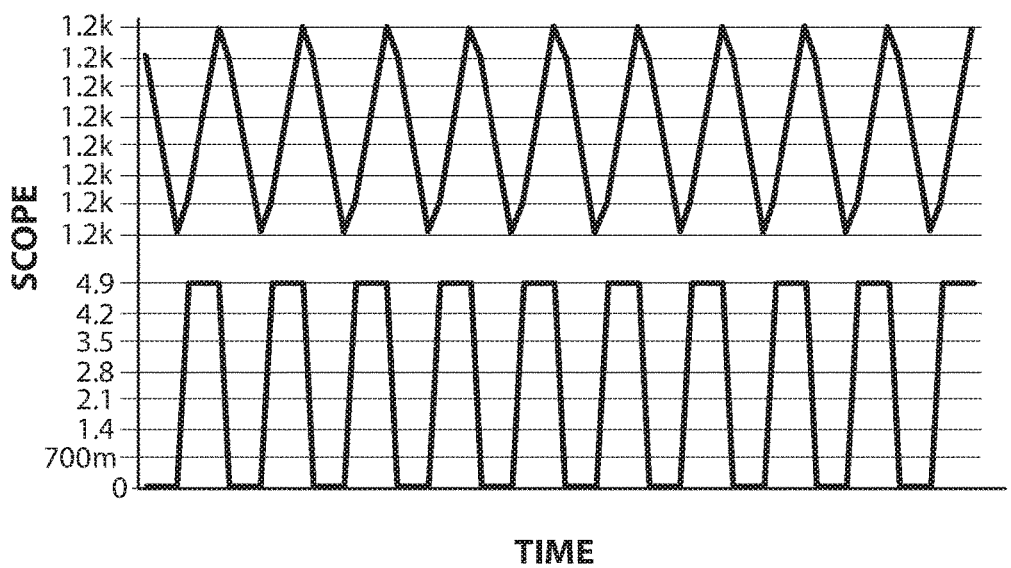
FIG. 14 is a graph of the output of a flyback convertor with 5V square wave input and a 1.25 KV RMS DC Output.
Figure 15:
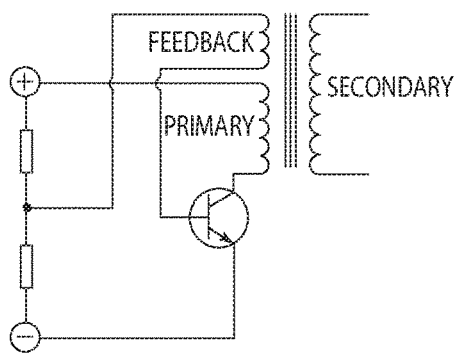
FIG. 15 is a schematic diagram of a flyback convertor using primary feedback to resonate.

As discussed above, high voltage power supplies are commonly used for cold plasma generation. Many ionizers or ion generators use a high voltage DC power supply which have traditionally been considered the most compact and economical. One typical method to create the high voltage charge for producing ions is to use a flyback converter using primary feedback to resonate. Variation of this circuit is shown in FIGS. 13 and 15. While simple and inexpensive, this approach has several disadvantages. First, the output voltage is not regulated and as such varies greatly while the circuit warms up. For some flyback convertors, the output may take up to 20 minutes for the output to stabilize. Even once warmed up, the output will still vary greatly with temperature or the input voltage, which is often unregulated.

In applications in close proximity to humans, it is desirable to have a well-regulated voltage output to ensure proper production of ions and to avoid production of compounds harmful to humans. For example, if the output drifts too high, arcing between the discharge points can occur causing a corona discharge that may produce ozone, which has been found to be harmful to humans if the amount of ozone exceeds certain threshold levels. Arcing or corona discharge may also occur between the discharge points and the metal of ductwork in heating, ventilation, and air conditioning systems, as well as appliances and fixtures. The sound caused by the arcing may be audible concern people in the proximity. Finally, this arcing can cause the ion generator to fail by melting conductors or otherwise damaging or degrading nearby components.

Figure 23:
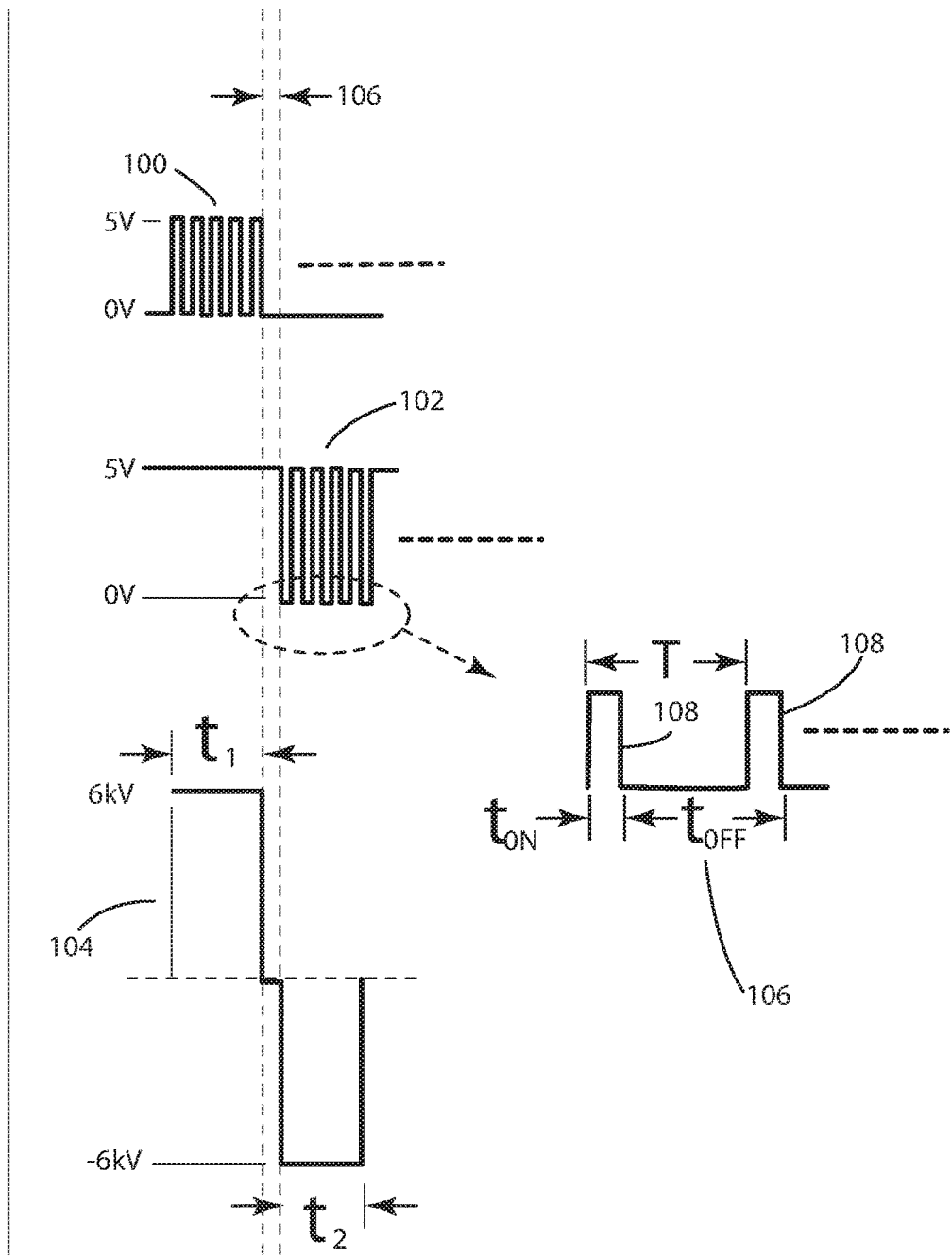
FIG. 23 illustrates an exemplary first drive signal and second drive signal and resulting high voltage AC voltage output.
Figure 24:
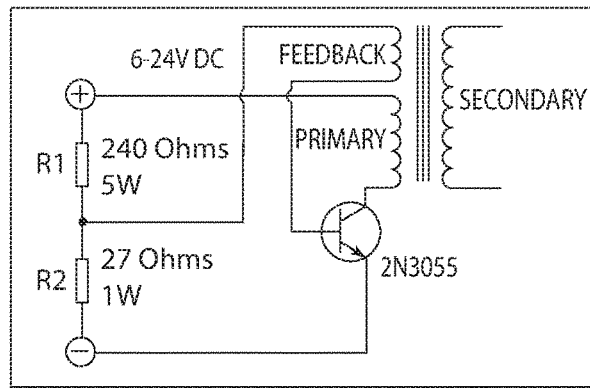
FIG. 24 illustrates a schematic diagram of a flyback convertor using primary feedback to resonate.
Figure 25:
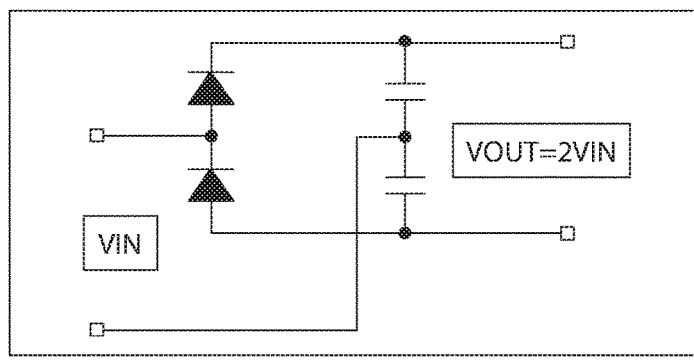
FIG. 25 illustrates a voltage multiplier circuit.
Figure 26:
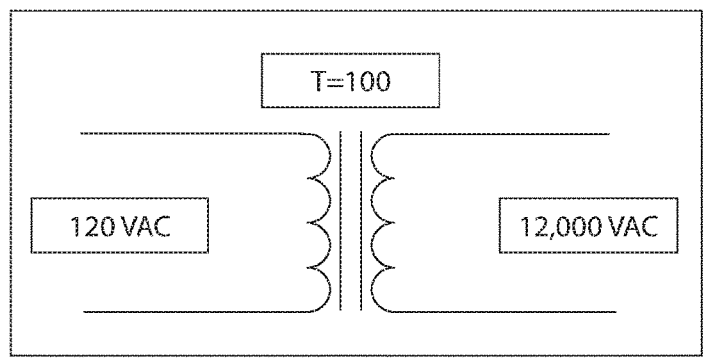
FIG. 26 illustrates a step-up transformer method of high voltage AC supply.
Figure 27:
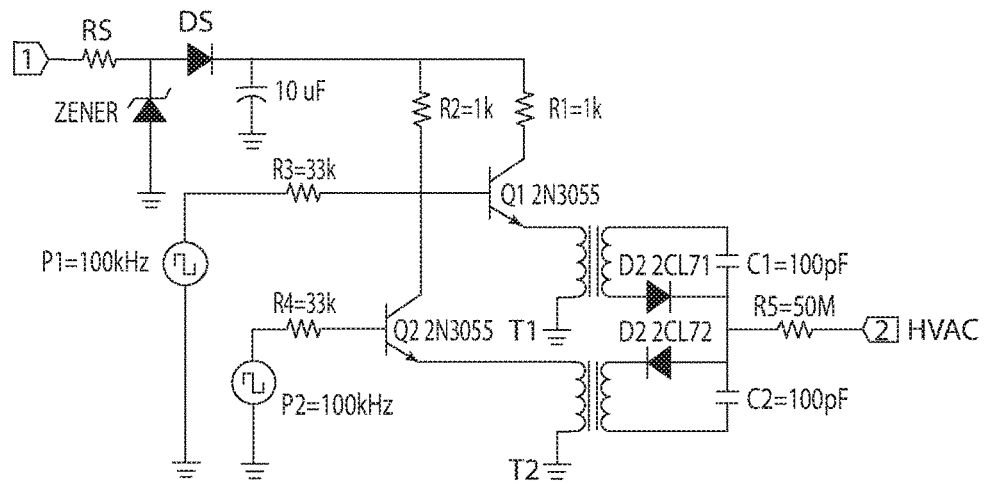
FIG. 27 illustrates a schematic diagram of a high voltage AC generator.

A regulated DC pulse provided to the primary winding of the flyback transformer may eliminate some of the above described issues. For example, the pulse may be controlled with a timing chip such as the LM555 or a microcontroller as illustrated in FIG. 23.

Figure 16:
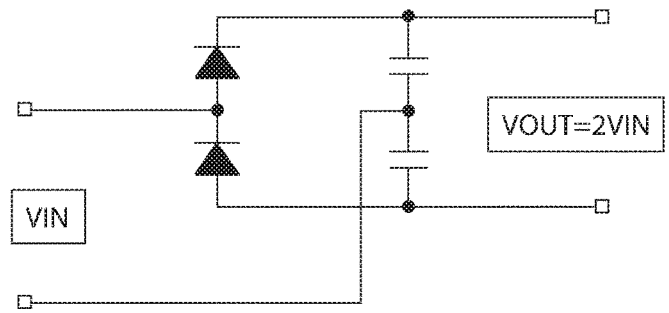
FIG. 16 is a voltage multiplier circuit which can be repeated for $V_{OUT}=X.VIN$.
Figure 17:
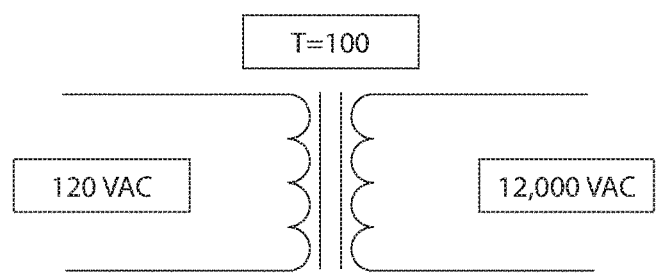
FIG. 17 is a step up transformer for high voltage AC supply.
Figure 18:
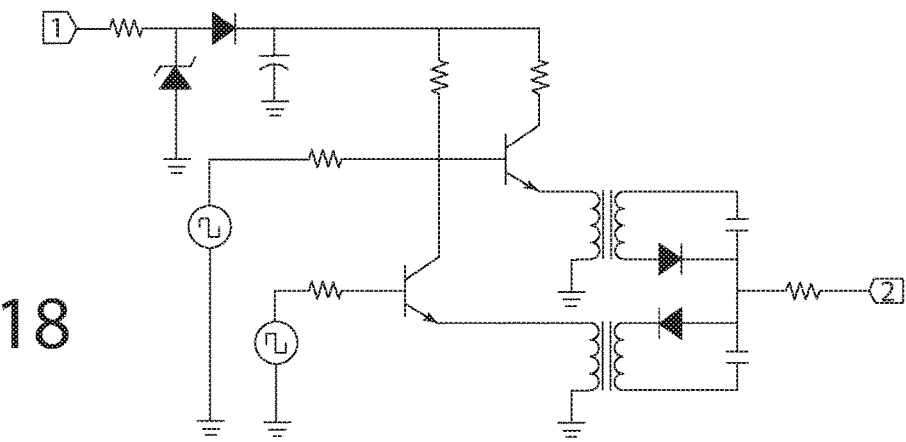
FIG. 18 is a schematic diagram of the ion generator using two flyback transformers.
Figure 19:
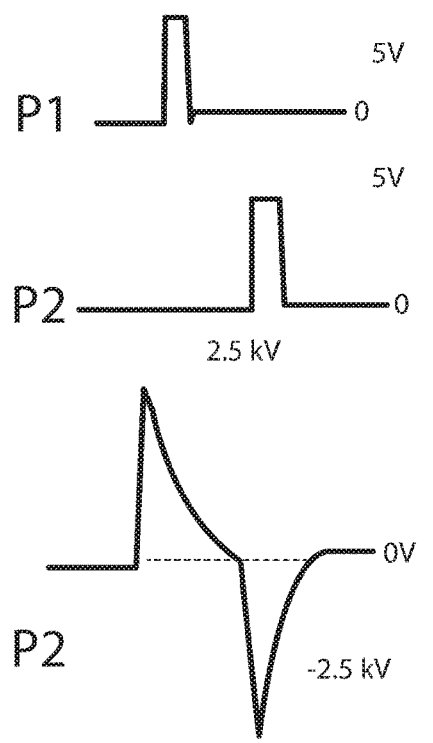
FIG. 19 is illustrates and exemplary input of P1 and P2 from the flyback transformers and the output on the ion electrode.

Another approach to create a high voltage is a voltage multiplier circuit, illustrated in FIG. 16. The input voltage can be AC or DC. However, the output will be DC, and over time, a DC output tends to collect dust, which reduces its ability to produce ions.

The flyback transformer can also be combined with a voltage multiplier to generate a higher output voltage. This approach is typically required when the secondary winding of the flyback transformer reaches the limits of its dielectric strength and cannot output a higher voltage without failure.

The battery may also be rechargeable, and the sanitizer 30 could include a USB port or other input that could provide charge to the battery. In addition, the device may include Bluetooth or Wi-Fi to allow control of the device with smartphones, computer, tablets, and the like, or for a person to check the status of all devices within a facility or within a given range. Control over the voltage output, and as such amount of ions generated as well as battery life could be controlled. Any inputs, such as a power supply input, USB input and the like may be covered to prevent liquid intrusion, such as if a sanitizer 30 was used on a kitchen counter.

As discussed above, most ion generators require a means of propulsion such as compressed air or $CO_2$ to move the ions away from the ion source, however, the inventors have surprisingly found that a high voltage AC ion generator is capable, of moving the ions away from the ion sources if properly configured and operated within certain operational ranges. In addition, the AC version described herein actually is an improvement in dispensing ions without separate means of propelling ions away from the ion sources as compared to traditional DC ion generators that use two electrodes, each have any opposing charge. The ion generator of the present invention creates more ions, uses less power, particularly less power from battery packs, and expels the ions a greater distance from the ion electrode without the need for additional propulsion, such as compressed gas in sanitizers. More specifically, an alternating current (AC) high voltage source has been found to be ideal for ion generators particularly when compared to traditional DC sanitizers. However, it should be noted that the DC sanitizer with the fork design overcomes the limitations of DC sanitizers particularly with regards to the fixture cavity as illustrated in FIGS. 1 and 3. One unique feature of the present invention is that the AC high voltage ion generator only requires one discharge electrode 80, which may have one or more points 84, not two discharge electrodes of opposite polarity, yet can function as a bipolar ion generator that generates both positive and negative ions. This single discharge point or single ion electrode 80 (which can have multiple discharge points 84 along the electrode as illustrated) can alternate between creating positive and negative ions. The inventors have found that this surprisingly yields the following advantages: (1) only one discharge point 84 required to create both positive and negative ions, although a ground electrode 90 may be still used to create a ground plane; (2) by alternating polarity of the single discharge point or ion electrode 80, it is far less likely to be contaminated with dust and will therefore have greater service life, because dust particles or other contaminants are attracted to the discharge point or electrode when it is positively charged will be repelled when it is negatively charged and vice versa; and (3) the use of AC high voltage ion generator can deliver higher concentrations of positive and negative ions at a greater distance from the discharge point(s) 84. The fact that the ion generating electrode 80 does not attract dust like the positive electrode of prior DC ion generators allows a longer service life and maintains operational performance closer to original specifications over the service life of the ion generator as the dust interferes on a DC ion generator with the generation of the positive ions. However, with regards to the illustrated DC sanitizer, the inventors have found that a burst of higher discharge may burn off dust particles, and while such a discharge may create ozone, the duration would be so short and so infrequent that barely any ozone would be created and would not noticeably add to the level of ozone in the proximity of the sanitizer and be under all applicable rules or regulations regarding the discharge of ozone. In addition, typically is was believed that to generate sufficient ions, at least two electrodes having opposing chargers were required, or at a minimum a sacrificial electrode was required. In the present invention, no sacrificial electrode is required, and the single ion electrode 80 generates all of the ions, and it is believed that the alternating current and resulting alternating production of positive and negative ions generates a pulse effect, similar to the ripples in water when an object is dropped in that as small waves expand outward.

In the present invention, the pulsing creates waves that cause the ions to travel away from the ion generating electrode.

While the ion generator of the present invention uses high voltage AC, which the stepped up or higher voltage AC is usually created using a step-up transformer, the step up transformer is not preferred as discussed below. In a step up transformer, a low voltage AC supply is supplied to the primary side of the transformer. The step-up transformer provides an output voltage that is equal to the input voltage multiplied by turns ratio of the step up transformer. For example, a transformer with 10 turns on the primary and 1,000 turns on the secondary has a turns ratio of 100 (T=100). If 120 VAC were applied to the input, the output voltage would be 12,000 VAC. While such a solution is simple and effective method for high voltage AC supply, it suffers from poor electrical efficiency, high cost, and large size.

Figure 28:
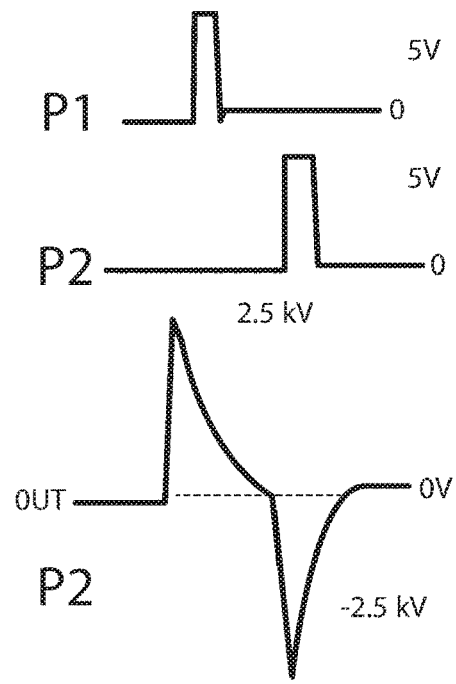
FIG. 28 illustrates an exemplary high voltage AC output.

Therefore, as stated above, the present invention can use a step up transformer, however the inventors have found it preferable to reduce the size of the packaging and the power loss due to heat generation. Therefore, the present invention creates high voltage AC for a single discharge point bipolar ionizer or multiple discharge points that experience the same positive or negative charge at the same time two flyback transformers 140, 142 resulting in a design which does not require the size, cost, weight, or energy consumption of a step-up transfer design. Further, the proposed design can accept a variety of AC or DC inputs to create the high voltage AC output. A simple pot can be provided to allow adjustment of the high voltage AC output for different applications. The range of AC output required to generate ions may vary, however the inventors have found that a minimum of 3000V peak to peak (e.g. +1500V to −1500V), preferably 4,000V peak to peak, and more preferably at least 5,000V peak to peak, but in no event more than 12,000V peak to peak, preferably less than 8000V peak to peak and more preferably less than 7500V peak to peak. The above voltages may vary depending on spacing and are set for the ion generating electrode 80 to be spaced between about 2 cm and 5 cm (¾"-2") from the ground plane or ground electrode 90. As such, for these spacings to avoid creating of ozone, the voltage ranges are critical, and as such, typically as the electrodes 70 are placed in closer proximity the lower end of the ranges above is preferred and as the spacing increases the higher end of the above voltage ranges is preferred. In addition, beyond strictly the distance, if the distance is a torturous pathway between the ion electrode 80 and the ground electrode 90, such as the illustrated puck design in the Figures, the voltage may be run at a higher voltage than if both of the electrodes were placed on the same surface with no intervening obstructions as the latter would be more likely to arc or create ozone. As it is best to balance power consumption and the amount of ions generating a range of voltage for the ion generating electrode to be spaced 2-5 cm from the ground electrode is typically 3,000-7,500V peak to peak, and preferably 4,000-6,000V peak to peak, and more preferably 5,000-6,000V peak to peak. As stated above, all of the voltage measurements provided are RMS voltage. As stated above, the present invention uses two flyback transformers 140, 142, one to create the positive half of a high voltage AC output and the other to create the negative half of the high voltage AC output. The two outputs are combined into a single high voltage AC output. A micro controller or microprocessor 144 is used to switch the transformers 140, 142 in a stable manner. The use of two flyback transformers that are switched also improves the output of the ion electrode 80, because the system is almost immediately at full power, maximizing production of the ions at the ion electrode 80, whereas a flyback transformer utilizing feedback from a primary or secondary coil to create a resonator does not stabilize to full power for a long period of time. FIG. 28 clearly illustrates the immediate spike in voltage over time against the square wave of the flyback transformers 140 and the slow drop off in voltage to the ion electrode 80 after the square wave has ended and then the immediate opposite jump in voltage as the square wave of the other flyback transformer 142 is applied. As the microcontroller 144 switches back and forth, the pattern is repeated. As illustrated in the Figures, a 5V input is provided and 2500 V output is then provided. Of course, other voltages, both output and input may be configured and provided.

The cycle rate between series of positive and negative peaks or drive signals 100, 102 (i.e., to provide the high voltage AC output) is preferably at least 10,000 Hz, and more preferably at least 25,000 Hz, and for the illustrated exemplary configuration in the Figures, the ion generator 110 operates at about 100,000 Hz, which provides the best balance of generating ions, low cost, and low power requirements. FIG. 23 illustrates exemplary drive signals 100, 102 and resulting high voltage AC output. It has been found that even with such quick cycling, the ions are sufficiently generated and the present invention typically uses 75,000-100,000 Hz frequency rate. It is important to note that the present invention does not use a 60 Hz cycle rate and more importantly that the present invention using an ion generator 60 operating at 100,000 Hz and 3000-7500V, preferably 5000-6000V peak to peak is operating at what many skilled in the art consider unstable and attempt to avoid. However, the inventors have surprisingly found that these parameters offer the best generation of ions, particularly when measured against the power consumption of the ion generator 60 where it is desired to maximize battery life.

FIG. 1 illustrates the sanitizer 30 including a fluid reservoir 120. The fluid reservoir 120 is configured to enhance but not replace the ion effect of the plasma field as the fluid passing through the plasma field creates a number of radicals that enhance the sanitizing effect and may even create a change in the composition of the fluid. It is important to note that the plasma field is not a thermal plasma field. More specifically with regards to the fluid in the fluid reservoir 120, if the fluid is water, water passing through the plasma field may create hydrogen peroxide, nitrates, various alcohols, hydroperoxy radicals, and nitric oxide radicals. As stated above, the fluid passing through the plasma field is only used to enhance the sanitizing effect as well as show a user that the sanitizer 30 is operating, such as in a hand sanitizer, when the user receives a small misting of fluid on their hands. Even with the fluid helping to sanitize the hands, a number of the ions generated are from the surrounding air or atmosphere. In addition, it should be noted that the ion generator 60, such as used in FIG. 1, does not use a thermal plasma and is safe for individuals to put their hands in close proximity or in even some circumstances, due to the safety safeguards of the sanitizer 30, touch or groundout the electrodes. As further illustrated in FIG. 1, a motion sensor system may be used to determine when to activate the discharge of fluid from the fluid reservoir, or as illustrated in FIG. 9, a simple switch may be used, which activates the ion generator and displays a desired amount of fluid from the fluid reservoir 120 and through or by the ion electrode 80. The sanitizer 30 may be covered by a housing 32 which includes a cover 50. FIGS. 29-31 illustrate a variation of the sanitizer 30 including a fluid reservoir 120, and the sanitizer 30 may be made in any style, shape or configuration.

Figure 2:
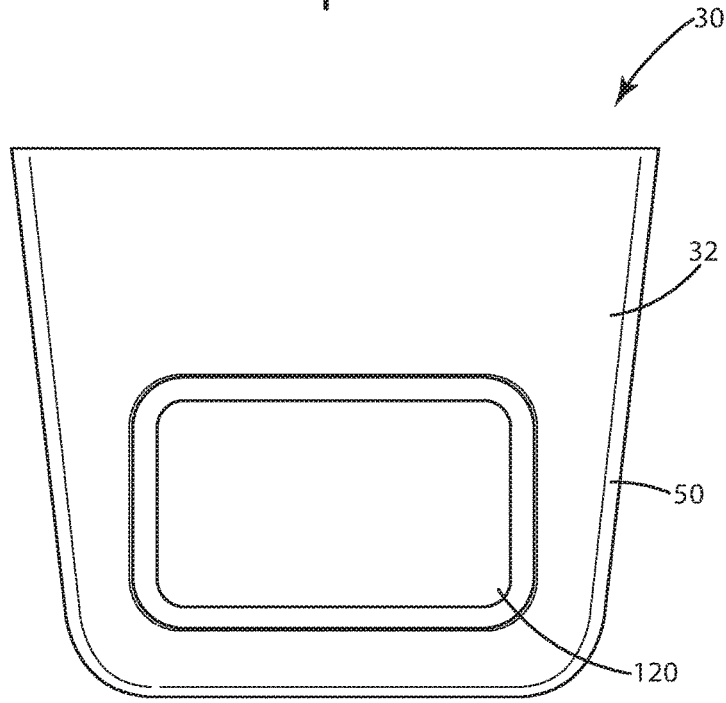
FIG. 2 is a top view of the sanitizer in FIG. 1.

FIG. 2 illustrates a top view of the sanitizer 30 in FIG. 41. The fluid reservoir 120 as well as the housing 32 and cover 50 may be formed in any size, shape or configuration and the style and configuration illustrated is only for illustrative purposes. Of course, the housing 32 and cover 50 could completely cover the fluid reservoir 120 which would allow the fluid reservoir 120 to be enclosed by the housing 32 and not visible to users. Of course, some fluid reservoir 120 may be replaceable with reservoirs that are prefilled with a fluid or refillable by the operator of the device or facility.

FIG. 3 illustrates the right side of the sanitizer 30 and the left side is substantially a mirror image thereof. FIG. 4 illustrates the bottom of the sanitizer 30, showing the outlet as well as the ion electrode 80 and the ion sources 82 spaced thereon, such as the illustrated points 84, and the nozzle 72 for generating the fluid that is configured to pass through the plasma field. Although not illustrated in FIG. 45, the ion electrode 80 may have an opposing ground electrode 90 spaced and located or attached to the housing 32. The ground electrode may also be formed from the nozzle, or may be connected through metal or conductive plastic as illustrated in FIG. 9. The connector 91 connects the ground electrode 90 to the controller 64. The ion electrode may also include a connector 81. The ground electrode 90 may also extend downward as illustrated in the Figures or be located near the control board 64 or inside the housing 32. Again, the housing 32 can take on a variety of sizes, shapes, and configurations and the illustrated shape and configuration should not be limited in the present invention. The nozzle 72, illustrated in FIG. 4, may be any type of nozzle capable of providing a spray or mist of the fluid from the fluid reservoir onto the hands or surface to be sanitized. As illustrated in FIG. 31, the nozzle 72 exits out the sides of the sanitizer 30, proximate to the ion electrode, such that fluid exiting the nozzles passes through the plasma field generated by the ion electrode. The nozzle may have many configurations, and may be used to fully atomize the fluid or in other embodiments provide a squirt such as a mist of fluid that is not fully atomized.

Figure 5:
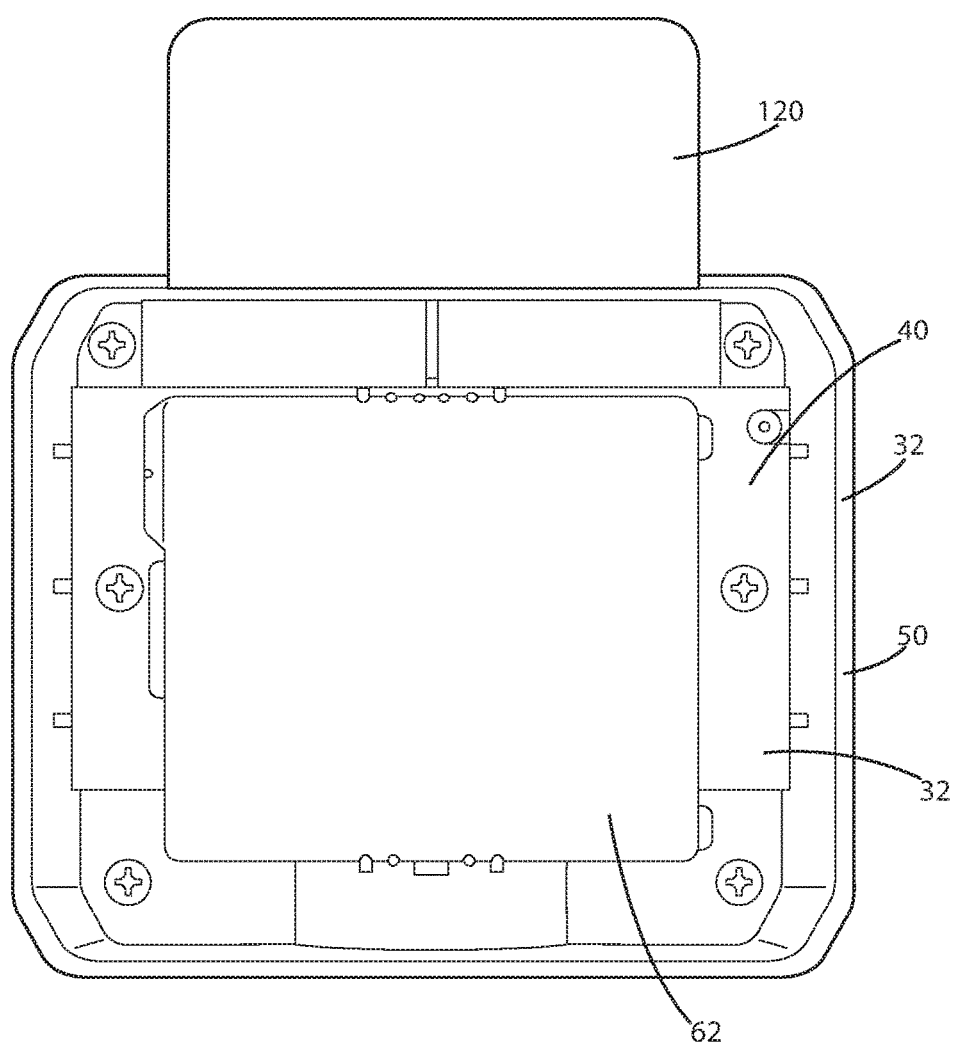
FIG. 5 is a back view of the sanitizer in FIG. 1.

As illustrated in FIG. 5, the back of the sanitizer 30 is shown which is normally attached to a wall or other support structure. In comparison, the sanitizer in FIGS. 29-31 may be adhered to almost any surface, such as a countertop used for food preparation, or a wall, although the passageway 122 between the fluid reservoir 120 and body of the sanitizer may need to be moved if the configuration of sanitizer 30 in FIGS. 29-30 is mounted on a vertical surface. The sanitizer 30, as illustrated in FIGS. 5 and 6 may include a backplate or base 40 which may in turn be secured to a wall or a wall bracket. Also illustrated in FIG. 6 is a battery case which will include a battery 62 for the ion generator 60. Of course, the battery in some embodiments may be used to drive the nozzle to activate upon sensing motion or in response to other controlled parameters, including time. The battery 62 may also be in a different size shape or configuration, as illustrated in FIGS. 30 and 31.

FIGS. 6, 9, 30, and 31 illustrate exploded perspective views of the sanitizer 30 with different configurations. While the cover 50 is illustrated as a two-part piece or as a single part piece and of course, it could be formed as a multi-part piece. The circuit board or controller 64 is illustrated in the Figures and is electronically coupled to the battery 62, motion sensor 36 (if included), and electrodes 70. If the controller 62 uses a DC system, two ion electrodes 80 are used, and if an AC system is used, an ion electrode 80 and ground electrode 90 are both used. The ion electrode 80, as illustrated, includes ion sources 82 such as points 84 which are helpful in distributing the ions as described above. The ion electrode may be formed of a polymeric material, such as described above a conductive polymeric material. Traditionally the ion electrodes were formed out of a single stainless steel needle, but the inventors have surprisingly found that contrary to the wisdom of a single point as a single ion source on an ion electrode, that multiple sources 82 that are points 84 is preferable and creates more ions in a better distribution pattern. The system may be controlled as a sanitizer 30 described above, and the sanitizer 30 includes a fluid reservoir 120. As illustrated, the sanitizer 30 foregoes the compressed gas cylinders, although they could be added in certain situations.

FIG. 7 illustrates a right sectional view taken along lines 7-7 in FIG. 1. The illustrated nozzle 72 is exemplary as well as the location of the ground strip or ground electrode 90. One skilled in the art should recognize that the conductive ground strip or electrode 90 may be formed of other materials as well as placed in a variety of other locations. In fact, the nozzle 72 itself in some embodiments may act as the ground electrode and as such, would be coupled to the circuit board or controller.

The sanitizer 30, and its components, as illustrated in FIGS. 1-31 may be used to clean hands such as in a medical setting, before food preparation, or in any other situation where it is desirable to kill fungi, bacteria, viruses or other pathogens. For example, in the medical setting, the sanitizer 30 is used before any procedure that requires sanitizing surfaces, instruments, and even hands, arms and other parts of the human body. In the food preparation setting, the sanitizer 30 may be used to sanitize hands when returning to the food preparation area, as well as the various items used in food preparation. In other settings, one may use the sanitizer 30 to sanitize hands or kill various pathogens including fungi, bacteria, viruses and other various unicellular organisms such as protozoa. In certain situations, the sanitizer 30 illustrated in FIGS. 1-31 may replace various chemical sanitizers and is generally effective at killing the various pathogens listed above without the use of chemicals or provided chemicals. Of course, one skilled in the art would recognize that with the addition of the fluid in some circumstances, some chemicals could be used, however, simply using water would generate additional radicals and change the content of the water such as at least partially to hydrogen peroxide which will provide additional sanitizing benefits. Therefore, while the ion generator 60 and sanitizer 30 illustrated in the Figures may be supplied and installed without any chemicals, the sanitizer 30 itself can produce various sanitizing radicals from the use of the fluid. Of course, the fluid enhances the ions generated by the plasma field and therefore, the ions generated by the plasma field also provide the sanitizing effect on the various surfaces to be sanitized. The fluid is used in addition to the ions being generated by the plasma field, not in place of the ions being generated by plasma field. As such, the sanitizer 30 still provides sanitizing of the desired surfaces even when the fluid runs out in the fluid reservoir, as the fluid only enhances the sanitizing effect of the sanitizer 30.

As discussed above, the sanitizer 30 could be used with a DC or AC driven ion sources, however, in each instance the sanitizer 30 uses a bipolar ionization particularly in connection with the AC driven ion generator 60. The plasma field also is a cold plasma or non-thermal plasma that is generated making the ion generator 60 generally safe for use in proximity near humans. The ion sources 82 are discharge points 84 on the ion electrode 80 which allow for the high frequency AC to discharge substantial amounts of ions at low power consumption creating an energy efficient ion generator 60 without the ion sources 82 being sacrificial. Therefore, the ion generator 60 generates plasma which may directly transmitted onto the hands, and the fluid or water mist of the sanitizer 30 increases the production of the OH radicals and the production of hydrogen peroxide in the plasma field, which may be misted on the hands to provide a user experience similar to chemical sanitizers such as alcohol based sanitizers. In addition, the plasma field as described above allows a dispersal of ions in a wave effect due to the high frequency AC generator which sanitizes the device itself as well as the space surrounding the sanitizer 30, including wall surfaces, mounting surfaces and even the floor underneath. In addition, as further described above, the ion sources 82 or discharged points 84 on the ion electrode 80 are current limited for safety by a 50 Mohm. The battery pack 62 may be formed from a variety of batteries that may be either replaced or recharged such as a lithium ion battery pack.

Figure 8:
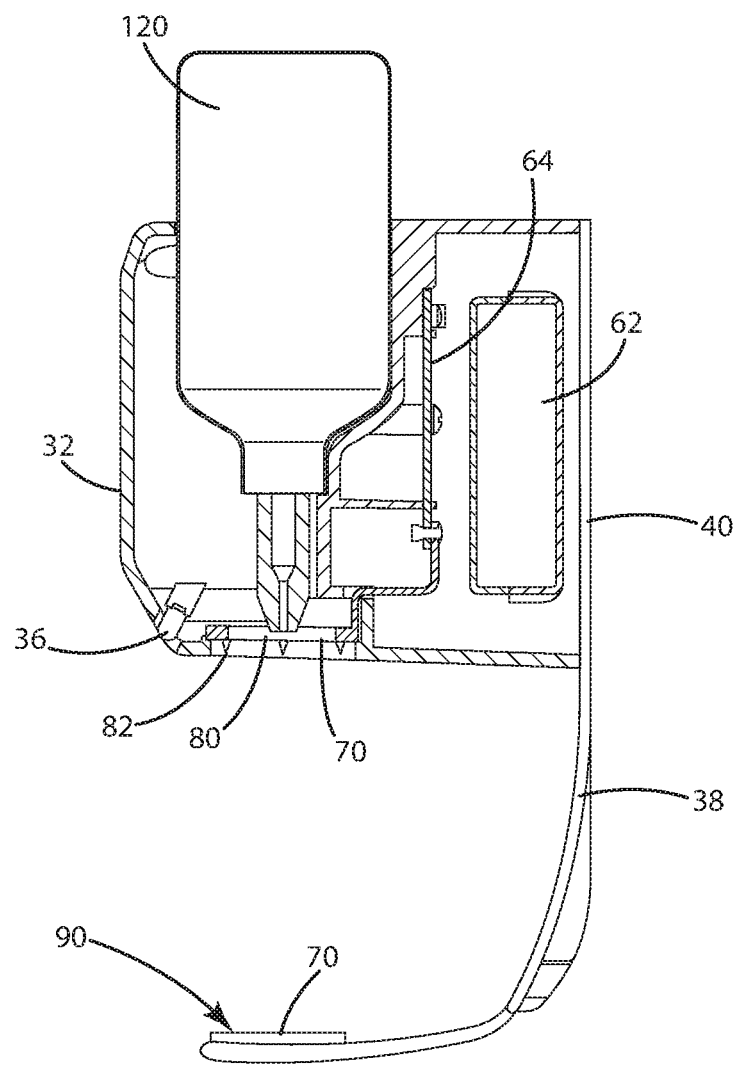
FIG. 8 is a sectional view of an exemplary sanitizer including a lower ground plane.

FIGS. 8 and 9 illustrate a sanitizer 30 having a backplate with a ground plane 90 extending outward on the backplate and displaced under and away from the ion electrode 80. The ground plane or ground electrode 90 being spaced away from the ion electrode 80 in a space where a user in a hand sanitizer would place their hands is configured to help extend the plasma field and direct the ions toward the ground plane. It should also be recognized that the ground plane 80 has an attraction for the source of the ions and is generally sanitized by the ions produced by the ion generator 60 from the ion electrode 80.

Many ion generators require the use of feedback to sense arcing or conditions which indicate that arcing is occurring at the emitter. Unstable output voltage can lead to arcing. Because of the stable high voltage output of the present invention, no feedback regarding arcing of self-discharge is necessary. Detection and feedback of self discharge adds additional components and complexity to the ion generator, therefore the overall cost of an ion generator can be reduced if feedback of self-discharge is avoided. It should be understood that self-discharge detection could however be implemented in the present invention if self discharge requirements are more stringent. One possible way to detect self discharge would be to monitor the output voltage.

Because the amount of airflow passing by the emitter of the present invention can also affect the amount of ionization which is necessary, a configuration of the present invention also includes an anemometer to measure the air velocity so that the output of the ion generator can be adjusted accordingly. Many current ion generators which are used in heating, ventilation, and air conditioning applications detect when a furnace or blower motor is turned on to determine when to adjust the ionization (e.g., increase as a result of more airflow). However, many newer heating, ventilation, and air conditioning systems now utilize variable speed motors, which may be on all of the time. One solution is to sense when the thermostat changes to a mode when it is actively heating or cooling based on a signal sent to the furnace or air conditioning, however signals may vary from different thermostats (i.e., could be between 15V-35V signal) and generally these signals are not intended for the purpose of controlling ion generators or other equipment so it may be possible to draw too much current. The anemometer may take the form of a pinwheel attached to a bar which includes the emitters within a duct. Although an anemometer may be used to measure air velocity, it should be appreciated that other ion generators may use other techniques or sensors for measuring air flow. Furthermore, experimental values of acceptable output voltages may be obtained for a given ion generator at various air velocities, stored in a look-up table, and later accessed by the microprocessor during operation of the ion generator to maintain optimal voltage levels for ionization while minimizing ozone production.

As mentioned, the present invention described above are less prone to contamination due to the emitter alternately emitting positive and negative ions causing so that dust particles or other contaminants are attracted to the emitter or electrode when it is positively charged will be repelled when it is negatively charged and vice versa. However, another configuration of the present invention includes a separate cleaning mode which intentionally creates a corona discharge to vaporize dust or contaminants on the emitter. Other ion generators may intentionally create ozone for short periods of time to help clean the emitter or area around the emitter.

In a separate ion generator for a heating, ventilation, and air conditioning application, multiple cold plasma generators are assembled together on an extruded mounting bar (see U.S. Pat. No. 8,873,215 B2). The mounting bar can be cut to the required length and an appropriate number of cold plasma generators or emitters are installed on the bar. It is desirable to have an ion generator with sharp discharge points along a variable length for many applications including a faucet sanitizer, door handle sanitizer, and needlepoint systems for heating, ventilation, and air conditioning. One approach has been to use carbon brushes. Each carbon brush has to be electrically connected via a wire which requires many separate parts including electrical connections and a housing. This is expensive and will not fit into small spaces. If a DC high voltage source is used, two of these assemblies are required doubling the cost and the space requirements. Another approach is to press fit stainless steel needled into a plastic dielectric pieces and devise a conductive piece to connect the needles. An additional housing is also needed. A similar approach is to injection mold conductive plastic pieces with sharp discharge points and connect with a conductive piece and a housing (see U.S. Pat. No. 8,861,167, US2013/0336838A1). These function well be are limited to being manufactured to a specific length that cannot be adjusted in the field (cut). Finally, another approach is to cut a flat sheet of stainless steel into a shape with multiple discharge points. An insulated housing is required. This may be seem more cost effective and use less space. However, care must be taken to radius every sharp edge except the sharp tips of the discharge points to prevent leakage that will damage the insulating housing and also ensure that the discharge points are producing ions at the desired level. Finally, the unit cannot be cut to length to fit a specific application. Cutting the device to a shorter length leaves sharp edges that will cause plasma discharge (leakage). Covering the sharp edges with an insulator will only result in the discharge damaging the insulator, and leaking ions where not desired, which reduces ion output where desired from the ion sources. The inventors have found that most insulative materials covering sharp edges are eaten through in a short time.

The emitters in the present invention are attached to a flexible circuit board such as a conductive and insulative tape. The inventors have discovered that it is possible to separately manufacture flexible circuit boards, flexible strips, or to modify commercially available LED light strips to provide both LED lighting and multiple points (emitters) or alternatively to provide spaced emitters 84 only. These LED strips generally include a conductive strip (e.g. copper)

laminated with urethane or other insulative material and affixed to a flexible polyamide dielectric material such as Kapton having a pressure sensitive adhesive disposed on one side to form a flexible circuit board. The points 84 are covered by the insulative material, such as the illustrated urethane dome on the top of the strip to protect the circuit and help support the emitters or needles. LEDs from the strip may be removed and replaced with emitters (e.g. stainless steel needles), which may be limited to select LEDs. The emitters may be pressed into the strip between LEDs or in place of LEDs and secured by various techniques, such as epoxy. The LEDs may be controlled by the microprocessor or by a separate controller. The LED strip in one ion generator may be single color LEDs, but a separate ion generator may use RGB multicolor LEDs so that the perceived color from the strip can be adjusted to a myriad of colors.

A high voltage low current source can be connected to one end of the strip with a suitable electrical connector. Ideally, the high voltage source is AC such that only a single row of connected discharge points is required. DC would require two rows of discharge points, one positive and one negative to create bipolar ionization along the separate conductive strip, or alternately a DC high voltage source could be connected to the single row of discharge points to create positive or negative ions only, not both. In one ion generator, the reference ground and emitter (high voltage output) is connected to the LED light strip or separately manufactured strip with emitters only. The high voltage AC output provides power to the emitters attached to the strip as well as the LEDs. The LEDs may be powered separately through a separate conductive pathway on the substrate.

The strips as described above may be mounted and used to sanitize, for example, a faucet, door handle, VFV/VRF (variable refrigerant flow/variable refrigerant volume) heating, ventilation, and air conditioning systems, traditional heating, ventilation, and air conditioning systems. Furthermore, it could be used for under cabinet lighting as a counter sanitizer, refrigerator lighting and sanitizing, sanitizing and lighting a bread box, or toy box. The flexible nature of the strips allow them to be installed any area that needs sanitizing and/or lighting. They even could be installed in vent outlets of vehicles, along ceilings of public transportation and restrooms and almost any other place where santizing is desired, limited only by imagination due to their size, flexibility, and low cost. The flexible discharge points described in this invention are flexible and very small. The strips can be cut to any length with simple scissors for each installation in any application.

As illustrated in FIGS. 32-42, the present invention is directed to a new ion electrode assembly 200. In developing this ion electrode assembly 200, a new ion generator 110 was also developed that surprising does not have a ground electrode 90 close in proximity to the ion electrode 80. More specifically, the ion generator 110 uses an earth ground, or a ground from the surrounding environment, machine, apparatus, or device. This new configuration surprisingly generates for more effective or useable ions for sanitizing than the devices where the ground electrode 90 is in close proximity to the ion electrode 80. It has been widely known that the closer the ground electrode 90 and ion electrode 80 are placed in proximity, the stronger the electrical field, and therefore, the more ions that are generated. However, it has been surprisingly found that when measured some distance away from the device, where the useable ions would occur that would perform the sanitizing, the number of useable ions is much greater, even given that a much weaker electrical field is generated, producing more ions when the ground electrode 90 is in the surrounding environment and not in close proximity with a specific ion electrode 80. This increase in ions is exactly opposite the teaching currently in the art.

In addition, the inventor has also surprisingly found that the ion sources 82 may be covered by a dome 184 of thin wall of dielectric material such as plastic, polymer, or glass or other insulative materials, thereby preventing injury for contact with the points 82, yet suprisingly still produce sufficient ions on the opposite side of the dome 184 from the points 82. Even though the ion generator 110 runs at a voltage that is not harmful to touch, enclosing the ion sources 82 and connective surfaces prevents any shorting of the ion electrode assembly 200 in a wide range of environments, including those that experience moisture, prevents injury from contact and prevents accumulation of dust and debris on the points 82, which reduces ion generation. Surprisingly the domes 184 still allow a generous amount of ions to pass through and in reality the ion electrode assembly disclosed herein provides sufficient ions in a compact, cost efficient and reliable package that substantially outperforms prior art devices with exposed electrode, in direct opposition to prior teachings. The domes 184 in FIGS. 32-37 and covers 202 in FIGS. 38-42 are formed from a dielectric or nonconductive material. If for example, the domes 184 and covers 202 are conductive and connected to ground, a large number of ions may result, however, ozone could be produced, which the present invention is configured to minimize, or prevent. Additionally, the domes 184 and covers 202 are preferably nonconductive, so that if they are not grounded, any risk of electric shock is reduced. In the present invention, the nonconductive material of the domes 184 and cover 202 has surprisingly been found to provide more useable ions at the location where the ions are desired, such as at a surface, hands, in the air in an HVAC system, over a coil in an HVAC system and the like. Placed in an HVAC system, such as before the filter, could prevent the filter from growing pathogens and other undesirable organisms, likewise placed proximate to the coil in and HVAC system that regularly experiences moisture, the present invention also prevents the growth of harmful pathogens and organisms which then can be spread by the HVAC system or may be placed near vent outlets to sanitize the air entering or leaving. It is well known that cool damp areas in HVAC systems can have harmful effect on people breathing the air from such HVAC systems. In addition, for ductless mini-split systems, there is very limited ability to filter the air, and typically no ability to put in an efficient free flowing filter that is capable of filtering out most pathogens. As stated above, the filters need to be frequently cleaned or changed, such as every two weeks on most systems and most users do not follow this schedule, which allows pathogens and unwanted organisms to grow on the filters. In view of the filtration limits with ductless mini-split systems, so it is even more important to keep the coil free from harmful organisms and pathogens.

As illustrated in FIGS. 32-37, the substrate 186 is formed from a flexible material, such as an LED light strip normally used for strictly lighting purposes, which allows reduction in shipping costs, as the material may be rolled, instead of being of a rigid length and causing high shipping costs and increased potential for damage during shipping. The substrate 186 generally includes a flexible base material and a flexible conductive material applied thereto. Another insulative layer or other layers may be added as desired. The ion sources 82 are in contact with the flexible conductive material. A substrate material that is nonconductive may be placed over the substrate 186 and over the ion sources 82. This material may include domes 184 or other shapes that may be injection molded to create an air gap over the ion sources 82 when assembled. Of course, the ion electrode assembly 200 could be formed without the substrate cover 204, the domes 184, or both. The ion electrode assembly 200 also includes a connector 72. Of course, modifications may be made to the ion electrode assembly 200 as to size, shape, configuration.

FIGS. 38-42 represent an ion electrode assembly 200 with a complete cover 202. While this will likely have greater volume in shipping, the non-conductive cover 202 provides the same function as the domes 184, and can be coupled to the substrate 186, adhered to it, or just slipped over it, for example. The substrate 186 may be formed from a flexible material, or may be formed from a rigid material, to which the ion sources 82 are attached. As illustrated, the substrate 186 is a metal plate with attached ion sources, such as through welding. The cover 202 is placed over the substrate 186 and a fastener 42, such as the illustrated connectors 72 and fasteners 42 may be used. This ion electrode assembly 200 is particularly useful in the duct work of an HVAC system, although the connector 72 and fasteners 42 need to be insulated from and not contact any metal ducts.

It should be noted that the covers 202 and domes 184 are only capable of being used with the ion generator 110 of the present invention having AC source applied to the ion sources 82. The AC system with the ion electrode assembly 200 creates a field that extends above and through the nonconductive domes 184 and covers 202, creating the ions in the air around the domes 184 and covers 202. One big benefit of this surprising revelation that sufficient ions are generated from ion sources 82 that are covered and not exposed to the environment is that it eliminates the need to clean the ion sources 82. In prior embodiments, the ion sources 82 would collect dust and debris that would substantially reduce their efficiency and require cleaning, or generation of ozone in a cleaning step. Cleaning of the needles 84 can cause injury from the sharp points, so the use of domes 184 and covers 202 that surprisingly do not reduce the efficiency of the ion fields is a major step forward in creating a maintenance free ion electrode assembly 200. While the ion sources 82 may be covered with a solid dielectric material, it has been found that eventually the ion sources 82 will burn a hole through the solid material, which opens them to the environment and opens them to moisture and dust which can reduce the efficiency. As such, the dome 184 or cover 202 has been developed, which creates and air gap, but surprisingly provides as good of an ion field outside of the cover 202 or dome 184. The air gap prevents the burning of holes through the cover 202 or domes 184, creating a seal over the ion sources 82 that protect them from moisture and dust, therefore making them maintenance free and maintaining their effectiveness even in dirty environments. It has also been found that the dome 184 or cover 202 causes the ions to be distributed over a wider area, causing a more effective ion field, with all the benefits listed above and creating a shock resistant barrier between the environment and the ion sources.

As best shown in FIGS. 45-52, an additional ion electrode assembly 300 is disclosed. The ion electrode assembly 300 includes at least one emitter unit 302 adapted for attachment to an ion generator (e.g., ion generator 110). At least one ion source 82 is attached to the at least one emitter unit 302 for emitting ions. An emitter cover 304 that may be rigid or flexible and has a thickness and extends from a proximal end 306 to a distal end 308 and defines an inner surface 310 that is continuous. A flexible emitter cover 304 can be advantageous in order to contour around ducts or parts of an HVAC system. The emitter cover 304 preferably encloses the at least one emitter unit 302 for protecting the at least one ion source 82 and the at least one emitter unit 302. However, it should be appreciated that the emitter cover 304 could instead only partially cover the at least one emitter unit 302 and/or at least one ion source 82. The inner surface 310 of the emitter cover 304 is in a spaced relationship with the at least one ion source 82 to define an air gap. It is preferred that the air gap is between 0.5 millimeters and 1.0 millimeters, however, other air gap dimensions may be utilized instead. The emitter cover 304, in this non-limiting example, is a tube of plastic. Nevertheless, it should be appreciated that other shapes and configurations of the emitter cover 304 may be used as well as various materials. However, as with the domes 184 and covers 202 discussed above, it is preferable for emitter cover 304 to be formed of dielectric or nonconductive material. Because, the emitter cover 304 is preferably nonconductive, the production of undesirable ozone can be minimized or eliminated. Also, by utilizing an nonconductive emitter cover 304, the risk of electrical shock is reduced, if for example, the emitter cover 304 is not grounded. While the inside surface 310 of the emitter cover 304 can be continuous (i.e., unbroken), the emitter cover 304 could instead be perforated (e.g., perforations 305 shown in FIGS. 50 and 51) Additionally, the thickness of the emitter cover 304 can be reduced by a predetermined amount proximate the at least one ion source 82. For example, the predetermined amount can be between 0.003 inches and 0.010 inches. Additionally, the emitter cover 304 could include a solid cover with a hose slipped over the at least one emitter unit 302. The at least one ion source 82 could then burn through the solid cover to create an air gap, while spacing the needles 82 from the hose or, so that the hose doesn't get burned through. Other spacing elements could be added around the points 82.

The ion electrode assembly 300 can also include at least one cover mount 312 coupled to the emitter cover 304 and adapted for attachment of the ion electrode assembly 300 to a surface with a fastener 42. A spacer 313 may also be used in conjunction with the fastener 42 and can be disposed about the fastener 42. Specifically, the fastener 42 can extend through the spacer 313 to position the ion electrode assembly 300 in a spaced relationship with the surface to which it may be mounted.

The at least one emitter unit 302 can include a plurality of emitter units 302 and each of the plurality of emitter units 302 extends from a first end 314 to a second end 316. Each of the plurality of emitter units 302 also includes a first electrode pad 318 disposed at the first end 314 and a second electrode pad 320 disposed at the second end 316 for electrically coupling to another of the plurality of emitter units 302. Additionally, the electrode pads 318, 320 are electrically coupled to the at least one ion source 82 (e.g., through a circuit trace or segment of conductive material). At least one jumper 322 may be used for interconnecting the first electrode pad 318 of one of the plurality of emitter units 302 and the second electrode pad 320 of another of the plurality of emitter units 302.

An end cap 324, preferably plastic, or other nonconducting material, has a cup shape is frictionally attached to the distal end 308 of the emitter cover 304 for sealing the distal end 308 of the emitter cover 304. An emitter electrical connector 326 is disposed about and attached to the proximal end 306 of the emitter cover 304 and adapted to accept at least one lead wire for attachment to the at least one emitter unit 302 adjacent the proximal end 306 of the emitter cover 304. The emitter electrical connector 326 can be sealed on the proximal end 306 of the emitter cover 304 with heat shrink tubing, for example. The emitter electrical connector 326 provides electrical power to the at least one emitter unit 302 from the ion generator 110. The ion electrode assembly 300 may be cut to any length by pulling off the end cap 324 cutting (e.g., with scissors) and replacing the end cap 324.

As best shown in FIGS. 53A-53C, the at least one ion source 82 includes a bottom portion 328 that has a circular shape. An emitter 84 that has a cone shape extends from the bottom portion 328. It should be appreciated that the at least one ion source 82 may take on various forms and configurations.

Figure 54:
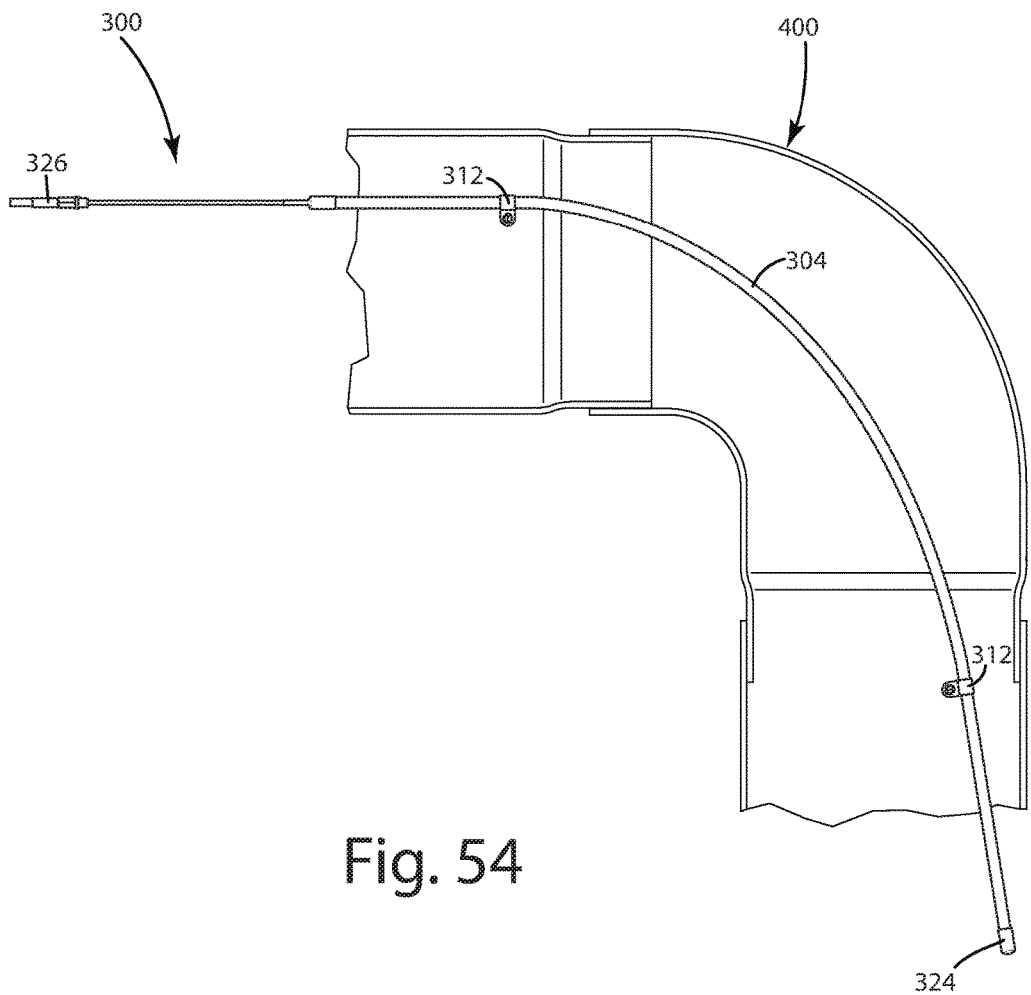
FIG. 54 is a perspective view of the ion electrode assembly of FIG. 45 installed in segment of ductwork.

Additionally, as best shown in FIG. 54, the ion electrode assembly 300 may be arranged in a curvilinear configuration. The ability of ion electrode assembly 300 to bend as needed allows the ion electrode assembly 300 to be installed in a segment of ductwork 400, for example.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. An ion electrode assembly comprising:
   at least one emitter unit adapted for attachment to an ion generator;
   at least one ion source attached to said at least one emitter unit for emitting ions;
   at least one emitter cover having a thickness and extending from a proximal end to a distal end and defining an inner surface being continuous and enclosing said at least one emitter unit for protecting said at least one ion source and said at least one emitter unit; and
   said inner surface of said emitter cover in a spaced relationship with said at least one ion source to define an air gap.

2. An ion electrode assembly as set forth in claim 1, wherein said at least one emitter cover is a tube.

3. An ion electrode assembly as set forth in claim 1, wherein said at least one ion source includes a plurality of ion sources and said at least one emitter cover is a plurality of domes each disposed about at least one of said plurality of ion sources.

4. An ion electrode assembly as set forth in claim 1, wherein said at least one emitter unit includes a plurality of emitter units and each of said plurality of emitter units extends from a first end to a second end and includes a first electrode pad disposed at said first end and a second electrode pad disposed at said second end for electrically coupling to another of said plurality of emitter units and said electrode pads are electrically coupled to said at least one ion source.

5. An ion electrode assembly as set forth in claim 4, further including at least one jumper for interconnecting said first electrode pad of one of said plurality of emitter units and said second electrode pad of another of said plurality of emitter units.

6. An ion electrode assembly as set forth in claim 1, wherein said at least one emitter cover extends from a proximal end to a distal end and said ion electrode assembly further includes an end cap having a cup shape frictionally attached to said distal end for sealing said distal end of said at least one emitter cover.

7. An ion electrode assembly as set forth in claim 1, wherein said at least one emitter cover extends from a proximal end to a distal end and said ion electrode assembly further includes an emitter electrical connector disposed about and attached to said proximal end of said at least one emitter cover and adapted to accept at least one lead wire for attachment to said at least one emitter unit adjacent said proximal end of said emitter cover and to provide electrical power to said at least one emitter unit from the ion generator.

8. An ion electrode assembly as set forth in claim 1, wherein said at least one emitter cover is nonconductive.

9. An ion electrode assembly as set forth in claim 1, wherein said at least one emitter cover is formed of a dielectric material.

10. An ion electrode assembly as set forth in claim 1, wherein said at least one emitter cover is plastic.

11. An ion electrode assembly as set forth in claim 1, wherein said at least one emitter cover is perforated.

12. An ion electrode assembly as set forth in claim 1, wherein said air gap is between 0.5 millimeters and 1.0 millimeters.

13. An ion electrode assembly as set forth in claim 1, wherein said thickness of said at least one emitter cover is reduced by a predetermined amount proximate said at least one ion source.

14. An ion electrode assembly as set forth in claim 13, wherein said predetermined amount is between 0.003 inches and 0.010 inches.

15. An ion electrode assembly as set forth in claim 1, wherein said at least one ion source includes a bottom portion having a circular shape and an emitter having a cone shape extending from said bottom portion.

16. An ion electrode assembly as set forth in claim 1, further including at least one cover mount coupled to said at least one emitter cover and adapted for attachment of said ion electrode assembly to a surface with a fastener.

17. An ion electrode assembly as set forth in claim 16, further including a spacer disposed about said fastener to position said ion electrode assembly in a spaced relationship with the surface.

18. An ion electrode assembly comprising:
   an ion generator;
   at least one emitter unit adapted for attachment to said ion generator;
   at least one ion source attached to said at least one emitter unit for emitting ions;
   an emitter cover having a thickness and defining an inner surface and enclosing said at least one emitter unit for protecting said at least one ion source and said at least one emitter unit; and
   said inner surface of said emitter cover in a spaced relationship with said at least one ion source to define an air gap.

19. An ion electrode assembly as set forth in claim 18, wherein said inner surface of said emitter cover is continuous.

20. An ion electrode assembly as set forth in claim 18, wherein said emitter cover is a tube.

21. An ion electrode assembly as set forth in claim 18, wherein said at least one emitter unit includes a plurality of emitter units and each of said plurality of emitter units extends from a first end to a second end and includes a first electrode pad disposed at said first end and a second electrode pad disposed at said second end for electrically coupling to another of said plurality of emitter units and said electrode pads are electrically coupled to said at least one ion source.

22. An ion electrode assembly as set forth in claim 21, further including at least one jumper for interconnecting said first electrode pad of one of said plurality of emitter units and said second electrode pad of another of said plurality of emitter units.

23. An ion electrode assembly as set forth in claim 18, wherein said at least one emitter cover extends from a proximal end to a distal end and said ion electrode assembly further includes an emitter electrical connector disposed about and attached to said proximal end of said emitter cover and adapted to accept at least one lead wire for attachment to said at least one emitter unit adjacent said proximal end of said emitter cover and to provide electrical power to said at least one emitter unit from the ion generator.

24. An ion electrode assembly as set forth in claim 18, wherein said emitter cover is nonconductive.

25. An ion electrode assembly as set forth in claim 18, wherein said at least one emitter cover is formed of a dielectric material.

26. An ion electrode assembly as set forth in claim 18, wherein said emitter cover is plastic.

27. An ion electrode assembly as set forth in claim 18, wherein said thickness of said emitter cover is reduced by a predetermined amount proximate said at least one ion source.

28. An ion electrode assembly as set forth in claim 18, wherein said at least one ion source includes a bottom portion having a circular shape and an emitter having a cone shape extending from said bottom portion.

29. An ion electrode assembly comprising:
at least one emitter unit adapted for attachment to an ion generator;
at least one ion source attached to said at least one emitter unit for emitting ions;
an emitter cover being flexible having a thickness and extending from a proximal end to a distal end and defining an inner surface being perforated and enclosing said at least one emitter unit for protecting said at least one ion source and said at least one emitter unit; and
said inner surface of said emitter cover in a spaced relationship with said at least one ion source to define an air gap.

30. An ion electrode assembly as set forth in claim 29, wherein said emitter cover is a tube.

31. An ion electrode assembly as set forth in claim 29, wherein said at least one emitter unit includes a plurality of emitter units and each of said plurality of emitter units extends from a first end to a second end and includes a first electrode pad disposed at said first end and a second electrode pad disposed at said second end for electrically coupling to another of said plurality of emitter units and said electrode pads are electrically coupled to said at least one ion source.

32. An ion electrode assembly as set forth in claim 31, further including at least one jumper for interconnecting said first electrode pad of one of said plurality of emitter units and said second electrode pad of another of said plurality of emitter units.

33. An ion electrode assembly as set forth in claim 29, wherein said at least one emitter cover extends from a proximal end to a distal end and said ion electrode assembly further includes an emitter electrical connector disposed about and attached to said proximal end of said emitter cover and adapted to accept at least one lead wire for attachment to said at least one emitter unit adjacent said proximal end of said emitter cover and to provide electrical power to said at least one emitter unit from the ion generator.

34. An ion electrode assembly as set forth in claim 29, wherein said emitter cover is nonconductive.

35. An ion electrode assembly as set forth in claim 29, wherein said at least one emitter cover is formed of a dielectric material.

36. An ion electrode assembly as set forth in claim 29, wherein said emitter cover is plastic.

37. An ion electrode assembly as set forth in claim 29, wherein said thickness of said emitter cover is reduced by a predetermined amount proximate said at least one ion source.

38. An ion electrode assembly as set forth in claim 29, wherein said at least one ion source includes a bottom portion having a circular shape and an emitter having a cone shape extending from said bottom portion.

39. An ion electrode assembly as set forth in claim 29, further including at least one cover mount coupled to said emitter cover and adapted for attachment of said ion electrode assembly to a surface with a fastener.

40. An ion electrode assembly as set forth in claim 39, further including a spacer disposed about said fastener to position said ion electrode assembly in a spaced relationship with the surface.

* * * * *